(12) United States Patent
Yabunouchi et al.

US009306173B2

(10) Patent No.: US 9,306,173 B2
(45) Date of Patent: *Apr. 5, 2016

(54) AROMATIC AMINE DERIVATIVE AND ELECTROLUMINESCENCE DEVICE USING THE SAME

(71) Applicant: Idemitsu Kosan Co., Ltd., Tokyo (JP)

(72) Inventors: Nobuhiro Yabunouchi, Chiba (JP); Tetsuya Inoue, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,307

(22) Filed: Oct. 29, 2015

(65) Prior Publication Data

US 2016/0049591 A1   Feb. 18, 2016

Related U.S. Application Data

(63) Continuation of application No. 14/838,414, filed on Aug. 28, 2015, which is a continuation of application No. 14/093,892, filed on Dec. 2, 2013, now Pat. No. 9,159,931, which is a continuation of application No. 13/360,513, filed on Jan. 27, 2012, now Pat. No. 8,623,522, which is a continuation-in-part of application No. 11/696,514, filed on Apr. 4, 2007, now Pat. No. 8,129,038.

(30) Foreign Application Priority Data

Apr. 26, 2006   (JP) .................................. 2006-121672

(51) Int. Cl.
*H01L 51/50* (2006.01)
*H01L 51/00* (2006.01)
*C07D 307/91* (2006.01)
*C07D 333/76* (2006.01)

(52) U.S. Cl.
CPC .......... *H01L 51/0061* (2013.01); *C07D 307/91* (2013.01); *C07D 333/76* (2013.01); *H01L 51/0073* (2013.01); *H01L 51/0074* (2013.01); *H01L 51/5056* (2013.01); *H01L 51/5088* (2013.01)

(58) Field of Classification Search
None
See application file for complete search history.

(56) References Cited

U.S. PATENT DOCUMENTS

| | | | |
|---|---|---|---|
| 6,517,957 B1 | 2/2003 | Senoo et al. | |
| 6,632,543 B1 | 10/2003 | Kawamura | |
| 7,998,596 B2 | 8/2011 | Yabunouchi et al. | |
| 2003/0118866 A1 | 6/2003 | Oh et al. | |
| 2004/0081853 A1 | 4/2004 | Conley | |
| 2004/0253389 A1 | 12/2004 | Suzuki et al. | |
| 2005/0208331 A1 | 9/2005 | Maeda | |
| 2006/0069287 A1 | 3/2006 | Kubo et al. | |
| 2006/0110623 A1 | 5/2006 | Funahashi et al. | |
| 2006/0159957 A1 | 7/2006 | Yabunouchi et al. | |
| 2006/0232198 A1 | 10/2006 | Kawamura et al. | |
| 2007/0296331 A1 | 12/2007 | Yabunouchi et al. | |
| 2008/0004445 A1 | 1/2008 | Hosokawa et al. | |
| 2009/0066239 A1 | 3/2009 | Yabunouchi | |
| 2009/0115320 A1 | 5/2009 | Kawamura et al. | |
| 2009/0302758 A1 | 12/2009 | Saitoh et al. | |
| 2010/0001636 A1 | 1/2010 | Yabunouchi | |
| 2011/0248217 A1 | 10/2011 | Tanabe et al. | |
| 2011/0278561 A1 | 11/2011 | Hosokawa et al. | |

FOREIGN PATENT DOCUMENTS

| | | |
|---|---|---|
| EP | 0 879 868 A2 | 11/1998 |
| JP | 4-11686 | 1/1992 |
| JP | 7-53955 | 2/1995 |
| JP | 8006266 | 1/1996 |
| JP | 8106167 | 4/1996 |
| JP | 8-231950 | 9/1996 |
| JP | 11-35532 | 2/1999 |
| JP | 11-111460 | 4/1999 |
| JP | 2001-011046 A | 1/2001 |
| JP | 2001288462 | 10/2001 |
| JP | 2001-354668 | 12/2001 |
| JP | 2002-88062 | 3/2002 |
| JP | 2003-129043 | 5/2003 |
| JP | 2003171366 | 6/2003 |
| JP | 3508984 | 1/2004 |
| JP | 2004-311415 A | 11/2004 |

(Continued)

OTHER PUBLICATIONS

Tai-Hsiang Huang, et al. "Organic electroluminescent derivatives containing dibenzothiophene and diarylamine segments" Journal of Materials Chemistry, 2005, vol. 15, No. 31, pp. 3233-3240, and a back page.
Japanese Office Action issued Jul. 17, 2012 in Patent Application No. JP2008-513112.

*Primary Examiner* — Gregory Clark
(74) *Attorney, Agent, or Firm* — Oblon, McClelland, Maier & Neustadt, L.L.P.

(57) ABSTRACT

Provided are a novel aromatic amine derivative having a specific structure and an organic electroluminescence device in which an organic thin layer comprising a single layer or plural layers including a light emitting layer is interposed between a cathode and an anode, wherein at least one layer of the above organic thin layer contains the aromatic amine derivative described above in the form of a single component or a mixed component. Thus, the organic electroluminescence device is less liable to be crystallized in molecules, improved in a yield in producing the organic electroluminescence device and extended in a lifetime.

23 Claims, No Drawings

(56) References Cited

FOREIGN PATENT DOCUMENTS

| JP | 2005044791 | 2/2005 |
| JP | 2005-112765 | 4/2005 |
| JP | 2005162620 | 6/2005 |
| JP | 2005-208110 | 8/2005 |
| JP | 2006-151844 | 6/2006 |
| JP | 2008-545729 | 12/2008 |
| JP | 2012-74707 A | 4/2012 |
| WO | WO 01/23344 A1 | 4/2001 |
| WO | WO 03/064373 A1 | 8/2003 |
| WO | WO 2004/040669 A1 | 5/2004 |
| WO | WO 2006/006505 A1 | 1/2006 |

AROMATIC AMINE DERIVATIVE AND ELECTROLUMINESCENCE DEVICE USING THE SAME

CROSS-REFERENCE TO RELATED APPLICATIONS

The present application is a continuation of U.S. patent application Ser. No. 14/838,414 filed Aug. 28, 2015, pending, which is a continuation of U.S. patent application Ser. No. 14/093,892 filed Dec. 2, 2013, U.S. Pat. No. 9,159,931, which is a continuation of U.S. patent application Ser. No. 13/360,513 filed Jan. 27, 2012, now U.S. Pat. No. 8,623,522, which is a continuation-in-part of U.S. patent application Ser. No. 11/696,514, filed on Apr. 4, 2007, now U.S. Pat. No. 8,129,038, which claims priority to Japanese patent application JP 2006-121672, filed on Apr. 26, 2006.

BACKGROUND OF THE INVENTION

The present invention relates to an aromatic amine derivative and an organic electroluminescence (EL) device obtained by using the same, more specifically to an organic EL device in which use of an aromatic amine derivative having a specific substituent for a hole transporting layer inhibits molecules from being crystallized to enhance a yield in producing the organic EL device and improves a lifetime of the organic EL device and an aromatic amine derivative which materializes it.

RELATED ART

An organic EL device is a spontaneous light emitting device making use of the principle that a fluorescent substance emits light by recombination energy of holes injected from an anode and electrons injected from a cathode by applying an electric field. Since organic EL device of a laminate type driven at a low voltage was reported by C. W. Tang et al. of Eastman Kodak Company (C. W. Tang and S. A. Vanslyke, Applied Physics Letters, Vol. 51, p. 913, 1987), researches on organic EL devices comprising organic materials as structural materials have actively been carried out. Tang et al. use tris(8-quinolinolato)aluminum for the light emitting layer and a triphenyldiamine derivative for the hole transporting layer. The advantages of a laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layered type comprising a hole transporting (injecting) layer, a light emitting layer and an electron transporting (injecting) layer are well known as the device structures of an organic EL device. In such laminate type structural devices, device structures and forming methods are studied in order to enhance a recombination efficiency of holes and electrons injected.

Usually, when an organic EL device is operated and stored under high temperature environment, brought about are adverse effects such as a change in a color of emitted light, a reduction in a current efficiency, a rise in an operating voltage and a reduction in an emission lifetime. A glass transition temperature (Tg) of a hole transporting material has to be raised in order to prevent the above matters. Accordingly, the hole transporting material has to have a lot of aromatic groups in a molecule (for example, aromatic diamine derivatives described in Patent document 1 and aromatic fused ring diamine derivatives described in Patent document 2), and usually, structures having 8 to 12 benzene rings are preferably used.

However, if they have a lot of aromatic groups in a molecule, crystallization is liable to be caused in forming a thin film using the above hole transporting materials to produce an organic EL device, and problems that an outlet of a crucible used for vapor deposition is clogged and that defects of a thin film originating in crystallization are caused to bring about a reduction in a yield of an organic EL device have been brought about. Further, compounds having a lot of aromatic groups in a molecule have usually a high glass transition temperature (Tg) but have a high sublimation temperature, and it is considered that the phenomena that decomposition is caused in vapor deposition and that a deposited film is unevenly formed are brought about, so that the problem that the lifetime is short has been involved therein.

On the other hand, a publicly known document in which asymmetric aromatic amine derivatives are disclosed is available. For example, aromatic amine derivatives having an asymmetric structure are described in Patent document 3, but no specific examples are found therein, and the characteristics of the asymmetric compounds are not described therein at all. Further, the examples of asymmetric aromatic amine derivatives having phenanthrene are described in Patent document 4, but they are handled on the same basis as symmetric compounds, and the characteristics of the asymmetric compounds are not described therein at all. Also, a specific synthetic process is required for the asymmetric compounds, but descriptions on the production processes of the asymmetric compounds are not clearly shown in the above patents. Further, a production process of aromatic amine derivatives having an asymmetric structure is described in Patent document 5, but the characteristics of the asymmetric compound are not described therein. Thermally stable asymmetric compounds having a high glass transition temperature are described in Patent document 6, but only examples of compounds having carbazole are shown.

Further, compounds having dibenzofuran are reported in Patent documents 7 to 13, but they assume a structure in which diamine compounds have dibenzofuran in a central skeleton thereof. Compounds having dibenzofuran at a terminal are reported in Patent documents 14 to 15, but they are monoamine compounds. Only specific examples are shown in Patent documents 8 to 12. Actual examples are described in Patent documents 7 and 14, but they are used only as photoconductors. An organic EL device is described in Patent document 13, but it does not have satisfactory performances.

As described above, organic EL devices having a long lifetime are reported, but they are not necessarily satisfactory. Accordingly, organic EL devices having more excellent performances are strongly required to be developed.

Patent document 1: U.S. Pat. No. 4,720,432
Patent document 2: U.S. Pat. No. 5,061,569
Patent document 3: Japanese Patent Application Laid-Open No. 48656/1996
Patent document 4: Japanese Patent Application Laid-Open No. 135261/1999
Patent document 5: Japanese Patent Application Laid-Open No. 171366/2003
Patent document 6: U.S. Pat. No. 6,242,115
Patent document 7: Japanese Patent No. 2501198
Patent document 8: Japanese Patent No. 2879370
Patent document 9: Japanese Patent No. 3508984

Patent document 10: Japanese Patent Application Laid-Open No. 34957/1993
Patent document 11: Japanese Patent Application Laid-Open No. 287408/1995
Patent document 12: Japanese Patent No. 3114445
Patent document 13: Japanese Patent Application Laid-Open No. 112765/2005
Patent document 14: Japanese Patent No. 3248627
Patent document 15: Japanese Patent Application Laid-Open No. 288462/2001

DISCLOSURE OF THE INVENTION

The present invention has been made in order to solve the problems described above, and an object thereof is to provide an organic EL device in which molecules are less liable to be crystallized and which is improved in a yield in producing the organic EL device and has a long lifetime and an aromatic amine derivative which materializes it.

Intensive researches repeated by the present inventors in order to achieve the object described above have resulted in finding that the above object can be achieved by using a novel aromatic amine derivative having a specific substituent represented by the following Formula (1) as a material for an organic EL device and using it particularly for a hole transporting layer, and thus the present inventors have come to complete the present invention.

Further, it has been found that an amino group substituted with an aryl group having a furan structure represented by Formula (2) or Formula (3) is suited as an amine unit having the specific substituent. The above amine unit has a steric hindrance, so that interaction between the molecules is small, and therefore it has the effects that crystallization thereof is inhibited to enhance a yield in producing an organic EL device and that the organic EL device obtained is extended in a lifetime. In particular, it has been found that a marked effect of extending the lifetime is obtained by combining with a blue color emitting device.

That is, the present invention provides an aromatic amine derivative represented by the following Formula (1):

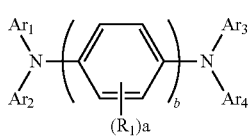

wherein $R_1$ is a hydrogen atom, a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 2 to 50 carbon atoms, an amino group substituted with a substituted or non-substituted aryl group having 5 to 50 ring carbon atoms, a halogen atom, a cyano group, a nitro group, a hydroxyl group or a carboxyl group; a is an integer of 0 to 4, and b is an integer of 1 to 3;
plural $R_1$ may be combined with each other to form a cyclic structure of a saturated or unsaturated five-membered ring or six-membered ring which may be substituted; at least one of $Ar_1$ to $Ar_4$ is represented by the following Formula (2) or (3):

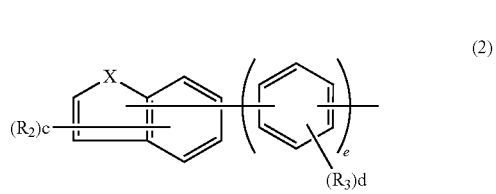

(wherein $R_2$ and $R_3$ each are selected independently from the same groups as those of $R_1$ in Formula (1) described above; X is oxygen, sulfur, selenium or tellurium;
c is an integer of 0 to 6; d is an integer of 0 to 3; and e is an integer of 1 to 3;
plural $R_2$ or $R_3$ may be combined with each other to form a cyclic structure of a saturated or unsaturated five-membered ring or six-membered ring which may be substituted;
when e is 2 or more and d is not 0, plural $R_3$ may be combined with each other to form a cyclic structure of a saturated or unsaturated five-membered ring or six-membered ring which may be substituted);

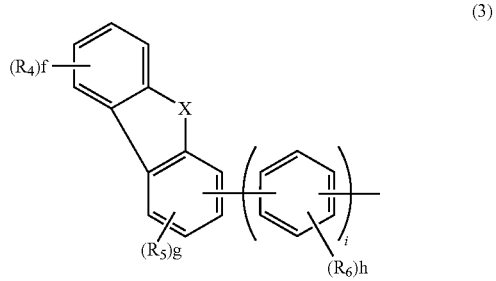

(wherein $R_4$ to $R_6$ each are selected independently from the same groups as those of $R_1$ in Formula (1) described above; X is an oxygen or sulfur atom;
f and h each are an integer of 0 to 4; g is an integer of 0 to 3; and i is an integer of 1 to 3;
plural $R_4$ or $R_5$ or $R_6$ may be combined with each other to form a cyclic structure of a saturated or unsaturated five-membered ring or six-membered ring which may be substituted;
when i is 2 or more and h is not 0, plural $R_6$ may be combined with each other to form a cyclic structure of a saturated or unsaturated five-membered ring or six-membered ring which may be substituted);
in Formula (1), among $Ar_1$ to $Ar_4$, the groups which are not represented by Formula (2) each are independently a substituted or non-substituted aryl group having 6 to 50 ring carbon atoms or a substituted or non-substituted aromatic heterocyclic group having 5 to 50 ring carbon atoms.

The present invention provides an aromatic amine derivative represented by the following Formula (5):

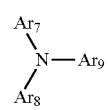

wherein at least one of $Ar_7$ to $Ar_9$ is represented by Formula (3) described above; in Formula (5), among $Ar_1$ to $Ar_3$, the groups which are not represented by Formula (3) each are independently a hydrogen atom, a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 2 to 50 carbon atoms, an amino group substituted with a substituted or non-substituted aryl group having 5 to 50 ring carbon atoms, a halogen atom, a cyano group, a nitro group, a hydroxyl group or a carboxyl group.

Further, the present invention provides an organic EL device in which an organic thin layer comprising a single layer or plural layers including a light emitting layer is interposed between a cathode and an anode, wherein at leas one layer of the above organic thin layer contains the aromatic amine derivative described above in the form of a single component or a mixed component.

Effect of the Invention

The aromatic amine derivative of the present invention and the organic EL device obtained by using the same are less liable to be crystallized in molecules, improved in a yield in producing the organic EL device and have long lifetimes.

BEST MODE FOR CARRYING OUT THE INVENTION

The aromatic amine derivative of the present invention is represented by the following Formula (1):

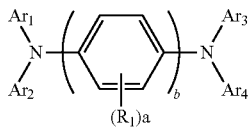

(1)

In Formula (1), $R_1$ is a hydrogen atom, a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 2 to 50 carbon atoms, an amino group substituted with a substituted or non-substituted aryl group having 5 to 50 ring carbon atoms, a halogen atom, a cyano group, a nitro group, a hydroxyl group or a carboxyl group.

In Formula (1), at least one of $Ar_1$ to $Ar_4$ is represented by the following Formula (2) or (3):

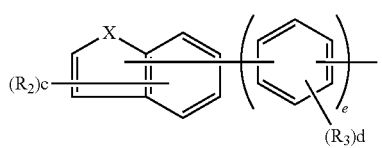

(2)

In Formula (2), $R_2$ and $R_3$ each are selected independently from the same groups as those of $R_1$ in Formula (1) described above. X is oxygen, sulfur, selenium or tellurium, and it is preferably an oxygen or sulfur atom, more preferably an oxygen atom.

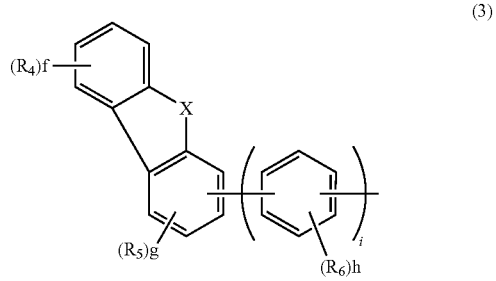

(3)

In Formula (3), $R_4$ to $R_6$ each are selected independently from the same groups as those of $R_1$ in Formula (1) described above. X is oxygen, sulfur, selenium or tellurium, and it is an oxygen or sulfur atom, preferably an oxygen atom.

The aryl groups represented by $R_1$ to $R_6$ in Formulas (1) to (3) include, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9- phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

Among them, preferred are phenyl, naphthyl, biphenyl, anthranyl, phenanthryl, pyrenyl, chrysenyl, fluoranthenyl and fluorenyl.

The alkyl groups represented by $R_1$ to $R_6$ in Formulas (1) to (3) include, for example, methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl and 2-norbornyl.

The alkoxy groups represented by $R_1$ to $R_6$ in Formulas (1) to (3) are groups represented by —OY, and the examples of Y include the same examples as explained in the alkyl group described above.

The aralkyl groups represented by $R_1$ to $R_6$ in Formulas (1) to (3) include, for example, benzyl, 1-phenyl ethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

The aryloxy groups represented by $R_1$ to $R_6$ in Formulas (1) to (3) are represented by —OY', and the examples of Y' include the same examples as explained in the aryl group described above.

The arylthio groups represented by $R_1$ to $R_6$ in Formulas (1) to (3) are represented by —SY', and the examples of Y' include the same examples as explained in the aryl group described above.

The alkoxycarbonyl groups represented by $R_1$ to $R_6$ in Formulas (1) to (3) are represented by —COOY, and the examples of Y include the same examples as explained in the alkyl group described above.

The examples of the aryl group in the amino group substituted with the aryl group represented by $R_1$ to $R_6$ in Formulas (1) to (3) include the same examples as explained in the aryl group described above.

The halogen atoms represented by $R_1$ to $R_6$ in Formulas (1) to (3) include a fluorine atom, a chlorine atom, a bromine atom and an iodine atom.

In Formula (1), a is an integer of 0 to 4, and b is an integer of 1 to 3, preferably 2. Plural $R_1$ may be combined with each other to form a cyclic structure of a saturated or unsaturated five-membered ring or six-membered ring which may be substituted.

In Formula (2), c is an integer of 0 to 6; d is an integer of 0 to 3; and e is an integer of 1 to 3, preferably 1. Plural $R_2$ or $R_3$ may be combined with each other to form a cyclic structure of a saturated or unsaturated five-membered ring or six-membered ring which may be substituted. When e is 2 or more and d is not 0, plural $R_3$ may be combined with each other to form a cyclic structure of a saturated or unsaturated five-membered ring or six-membered ring which may be substituted.

In Formula (3), f and h each are an integer of 0 to 4; g is an integer of 0 to 3; and i is an integer of 1 to 3, preferably 1. Plural $R_4$ or $R_5$ or $R_6$ may be combined with each other to form a cyclic structure of a saturated or unsaturated five-membered ring or six-membered ring which may be substituted. When i is 2 or more and h is not 0, plural $R_6$ may be combined with each other to form a cyclic structure of a saturated or unsaturated five-membered ring or six-membered ring which may be substituted.

The above cyclic structure of a five-membered ring or a six-membered ring which may be formed includes, for example, cycloalkanes having 4 to 12 carbon atoms such as cyclopentane, cyclohexane, adamantane, norbornane and the like, cycloalkenes having 4 to 12 carbon atoms such as cyclopentene, cyclohexene and the like, cycloalkadienes having 6 to 12 carbon atoms such as cyclopentadiene, cyclohexadiene and the like and aromatic rings having 6 to 50 carbon atoms such as benzene, naphthalene, phenanthrene, anthracene, pyrene, chrysene, acenaphthylene and the like.

The aromatic amine derivative of the present invention represented by Formula (1) has 42 or more carbon atoms, preferably 54 or more carbon atoms and more preferably 60 to 80 carbon atoms in terms of the total of carbon atoms excluding those of the substituents.

In the aromatic amine derivative of the present invention, $Ar_1$ and $Ar_2$ in Formula (1) described above are represented preferably by Formula (2) or Formula (3) described above.

In the aromatic amine derivative of the present invention, $Ar_1$ and $Ar_3$ in Formula (1) described above are represented preferably by Formula (2) or Formula (3) described above.

In the aromatic amine derivative of the present invention, only $Ar_1$ in Formula (1) described above is represented preferably by Formula (2) or Formula (3) described above.

In the aromatic amine derivative of the present invention, b in Formula (1) described above is preferably 2.

In the aromatic amine derivative of the present invention, f in Formula (2) described above is preferably 1.

In the aromatic amine derivative of the present invention, i in Formula (3) described above is preferably 1.

In the aromatic amine derivative of the present invention, X in Formula (2) described above is preferably an oxygen atom.

In the aromatic amine derivative of the present invention, $Ar_2$ in Formula (1) described above is represented preferably by the following Formula (4):

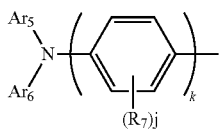

(4)

In Formula (4), $R_7$ is selected from the same groups as those of $R_1$ in Formula (1) described above, and the specific examples thereof include as well the same groups as the examples of $R_1$ to $R_6$ in Formulas (1) to (3).

In Formula (4), j is an integer of 0 to 4; and k is an integer of 1 to 3. Plural $R_7$ may be combined with each other to form a cyclic structure of a saturated or unsaturated five-membered ring or six-membered ring which may be substituted. When k is 2 or more and j is not 0, plural $R_7$ may be combined with each other to form a cyclic structure of a saturated or unsaturated five-membered ring or six-membered ring which may be substituted. In the above case, the specific examples of the cyclic structure of a five-membered ring or a six-membered ring include as well the same ones as the examples of $R_1$ to $R_6$.

$Ar_6$ and $Ar_7$ each are independently a substituted or non-substituted aryl group having 6 to 50 ring carbon atoms or a substituted or non-substituted aromatic heterocyclic group having 5 to 50 ring carbon atoms. The specific examples of the above aryl group or aromatic heterocyclic group include the same groups as the examples of the aryl groups represented by $R_1$ to $R_6$.

In the aromatic amine derivative of the present invention, $Ar_2$ and $Ar_4$ in Formula (1) described above each are preferably represented independently by Formula (4) described above.

The aromatic amine derivative of the present invention is represented by the following Formula (5):

(5)

In Formula (5), at least one of $Ar_7$ to $Ar_9$ is represented by Formula (3) described above, and among $Ar_1$ to $Ar_3$, the groups which are not represented by Formula (3) each are independently a hydrogen atom, a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 2 to 50 carbon atoms, an amino group substituted with a substituted or non-substituted aryl group having 5 to 50 ring carbon atoms, a halogen atom, a cyano group, a nitro group, a hydroxyl group or a carboxyl group. The specific examples thereof include as well the same groups as the examples of $R_1$ to $R_6$.

The aromatic amine derivative of the present invention is preferably a material for an organic electroluminescence device.

The aromatic amine derivative of the present invention is preferably a hole transporting material for an organic electroluminescence device.

The aromatic amine derivative of the present invention is preferably a hole injecting material for an organic electroluminescence device.

The aromatic amine derivative of the present invention is preferably a material having the functions of a hole injecting material and a hole transporting material for an organic electroluminescence device in combination.

In the organic electroluminescence device of the present invention in which an organic thin layer comprising a single layer or plural layers including at leas a light emitting layer is interposed between a cathode and an anode, at leas one layer of the above organic thin layer contains preferably the aromatic amine derivative of the present invention described above in the form of a single component or a mixed component.

In the organic electroluminescence device of the present invention, the aromatic amine derivative of the present invention described above is contained preferably in a hole transporting layer.

In the organic electroluminescence device of the present invention, the aromatic amine derivative of the present invention described above is contained preferably in a hole injecting layer.

In the organic electroluminescence device of the present invention, styrylamine and/or arylamine are contained preferably in a light emitting layer.

In the organic electroluminescence device of the present invention, light of a blue color is preferably emitted.

The specific examples of the aromatic amine derivative of the present invention represented by Formula (1) are shown below, but they shall not be restricted to these compounds shown as the examples.

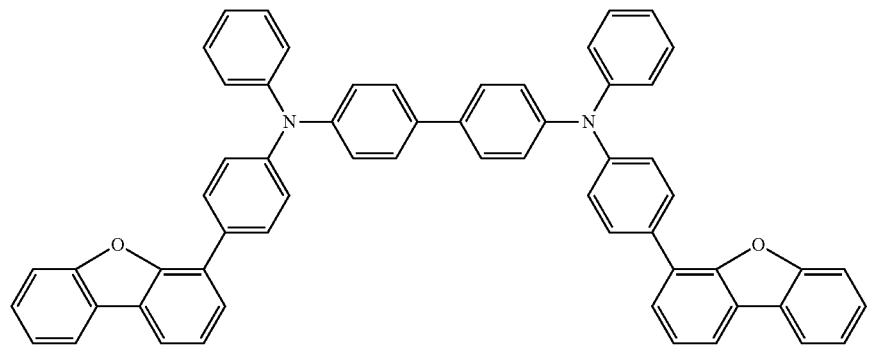
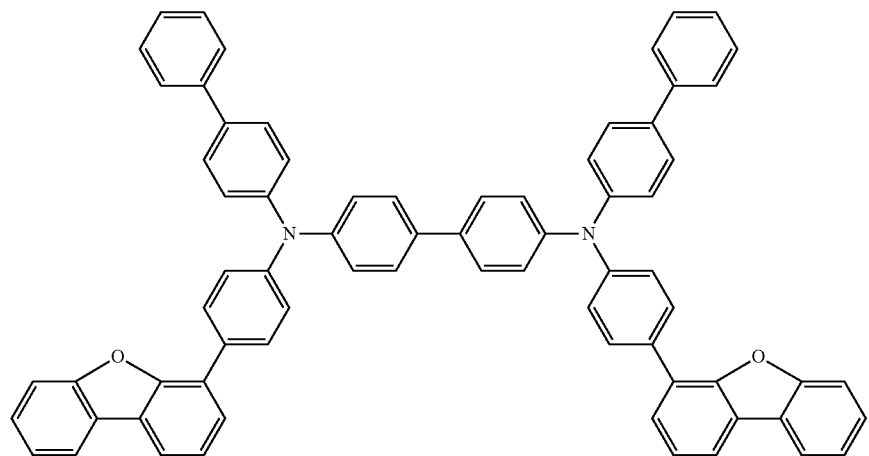
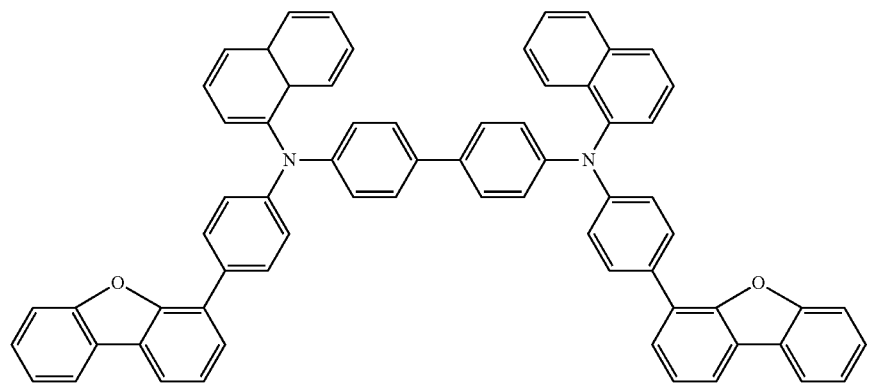
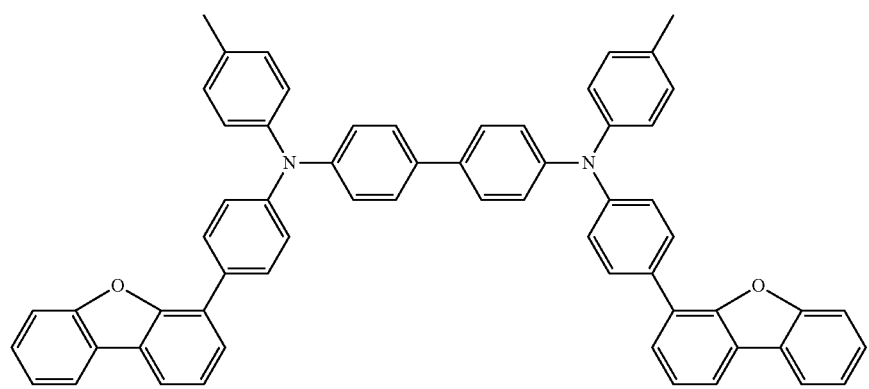

-continued
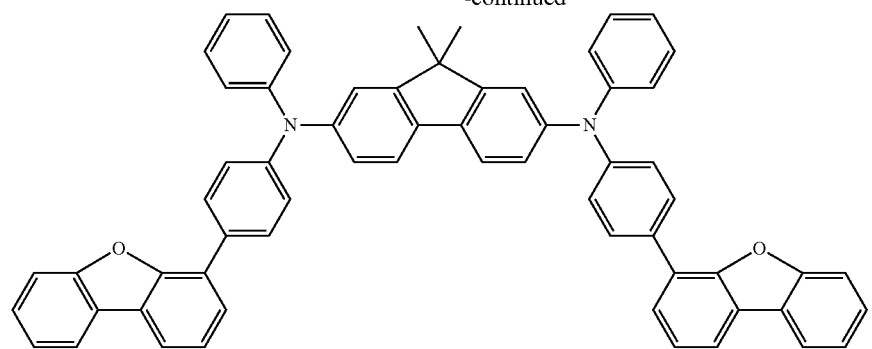
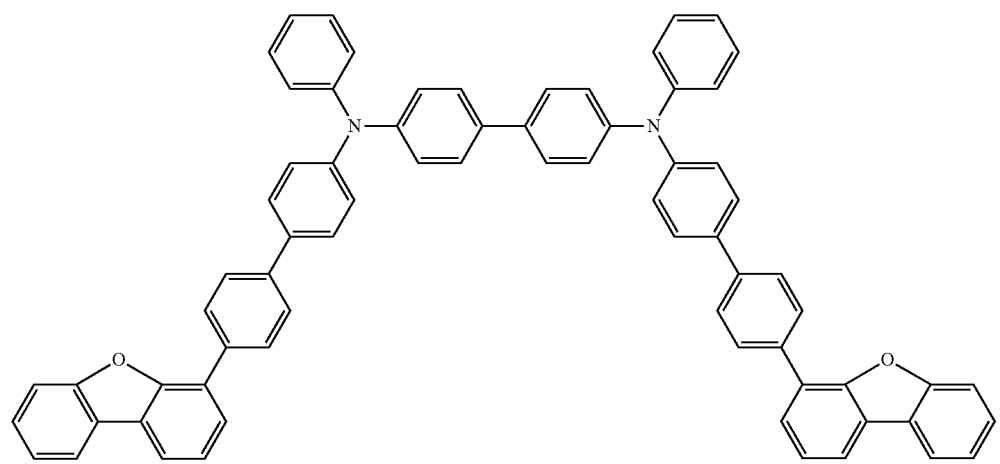
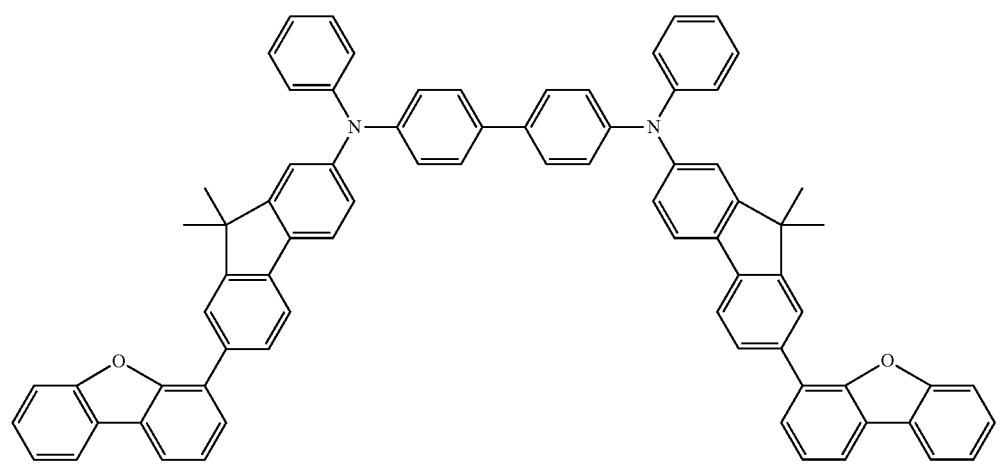
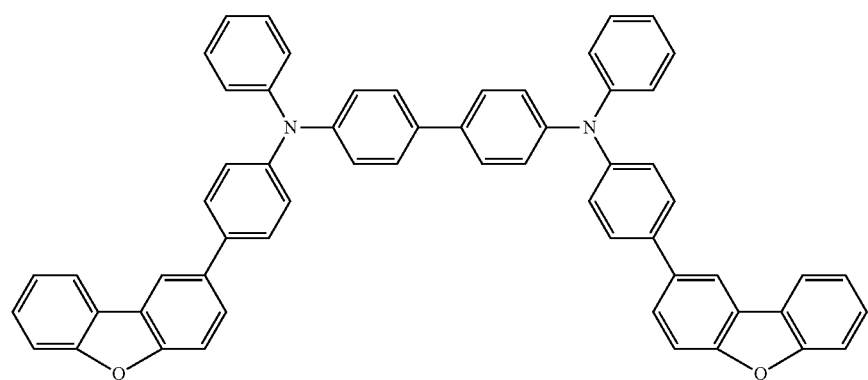

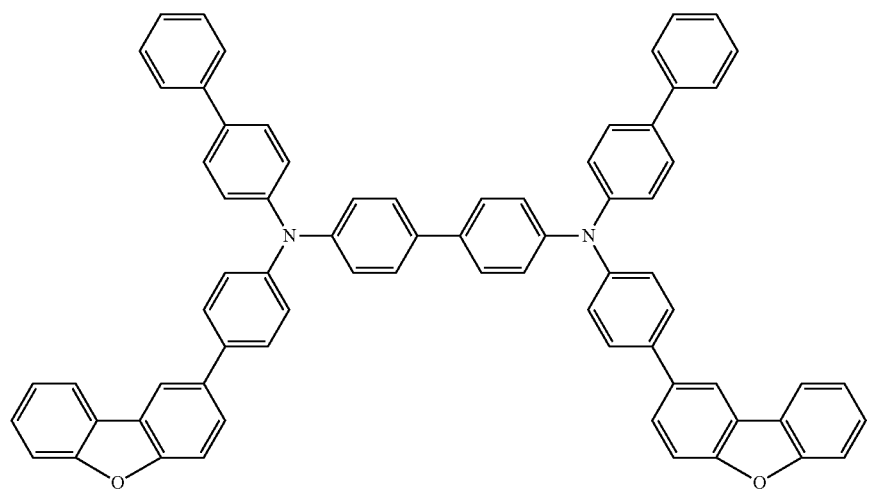
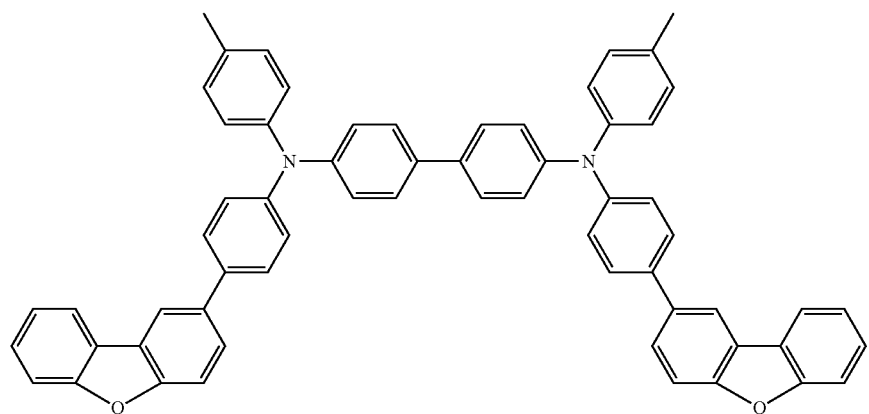
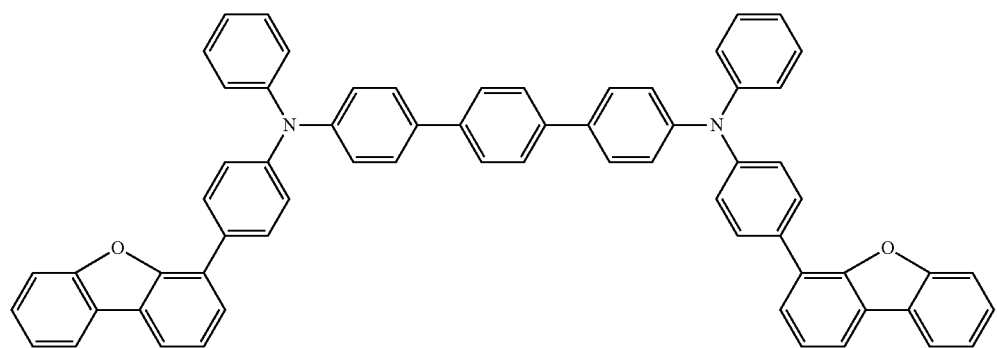

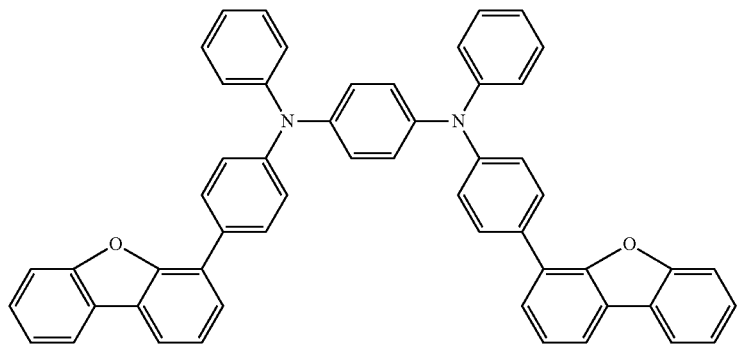
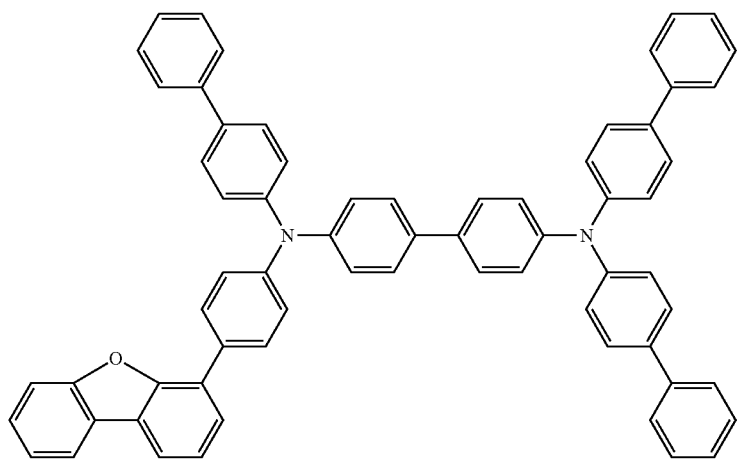
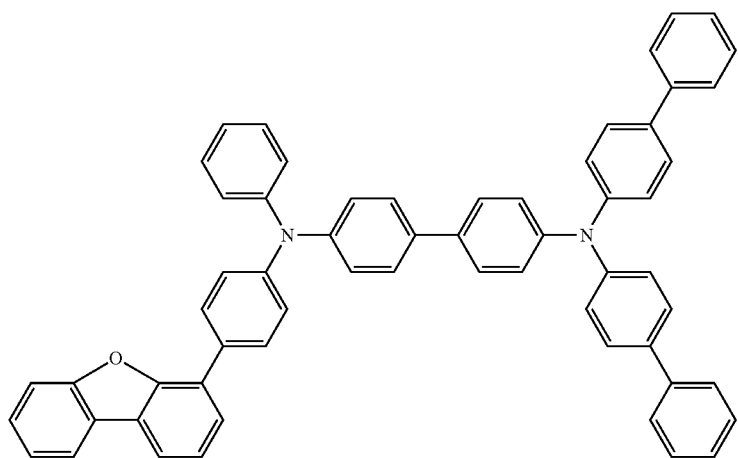

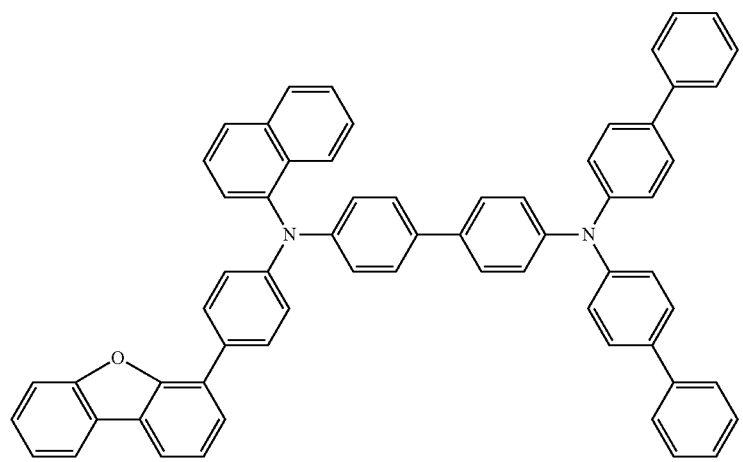
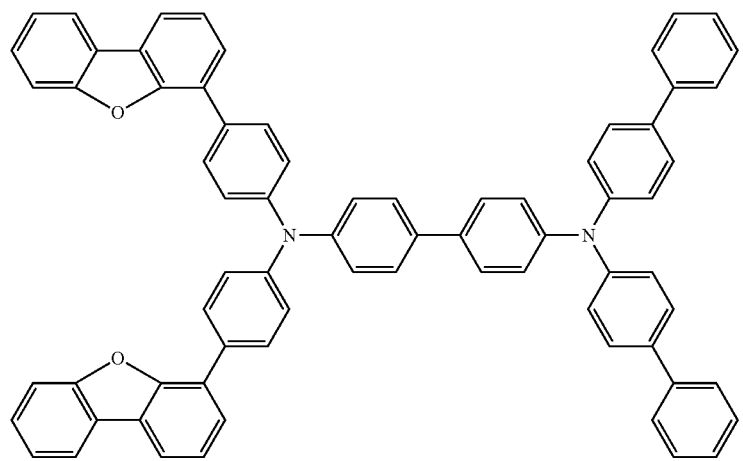
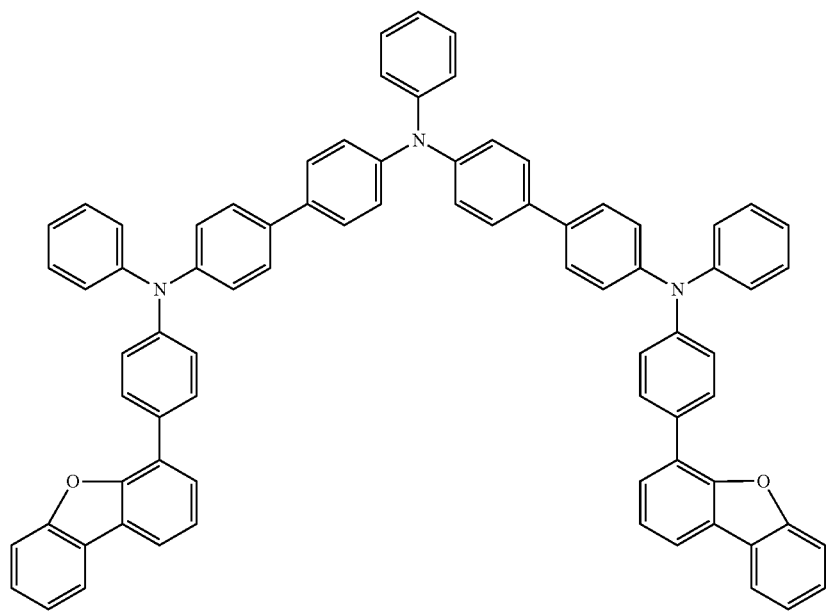

-continued
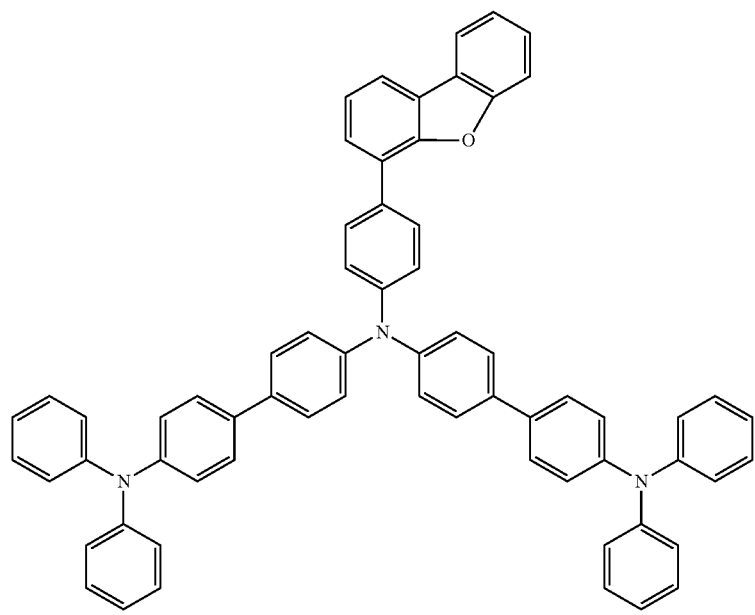
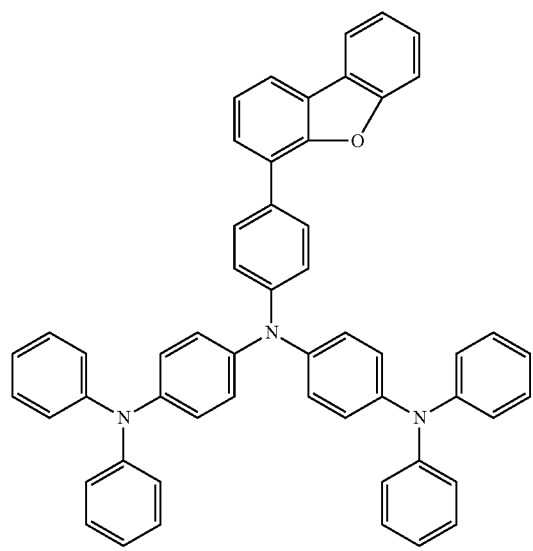

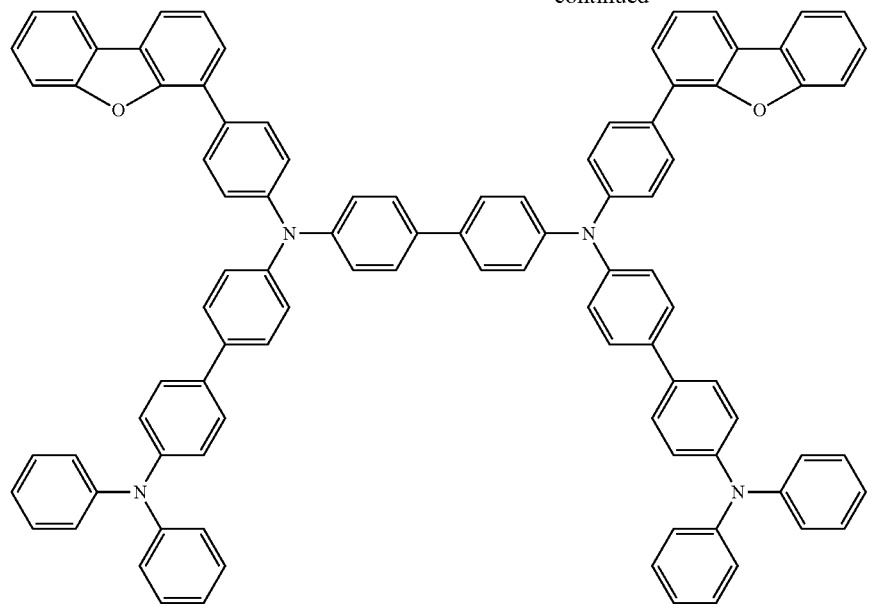
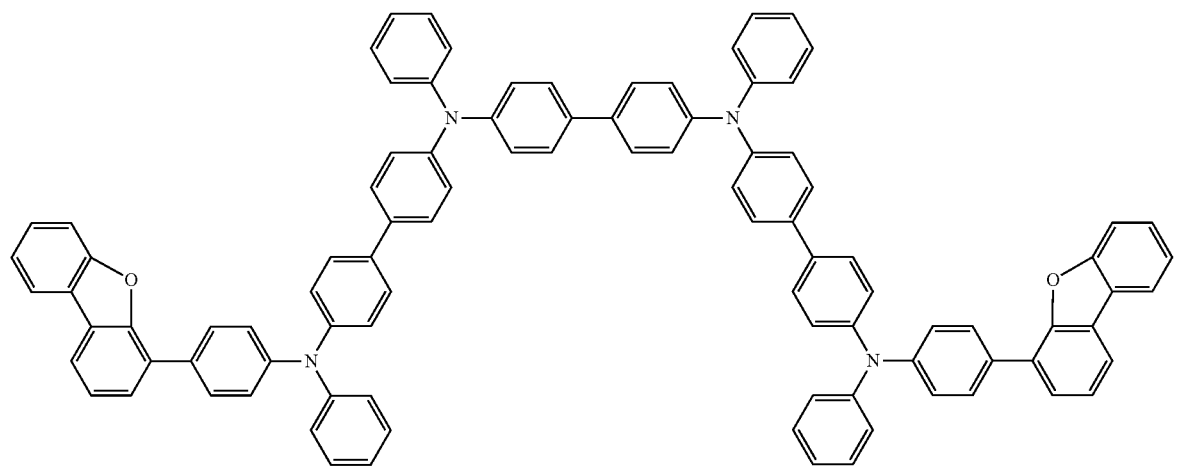
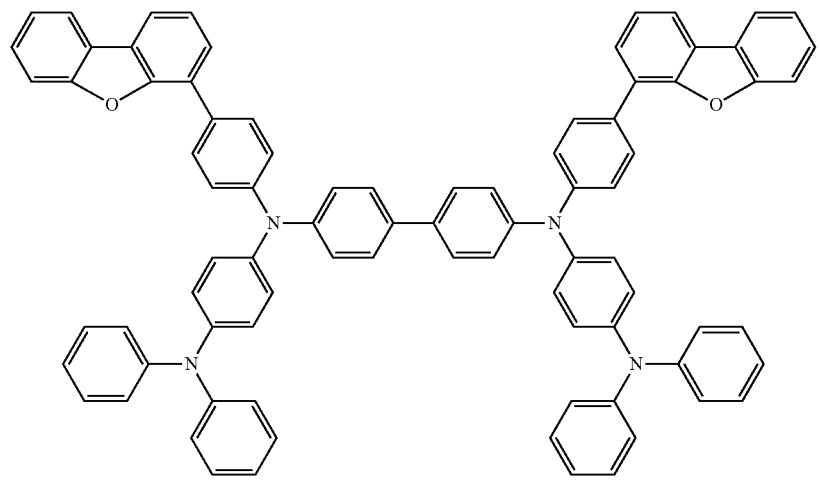

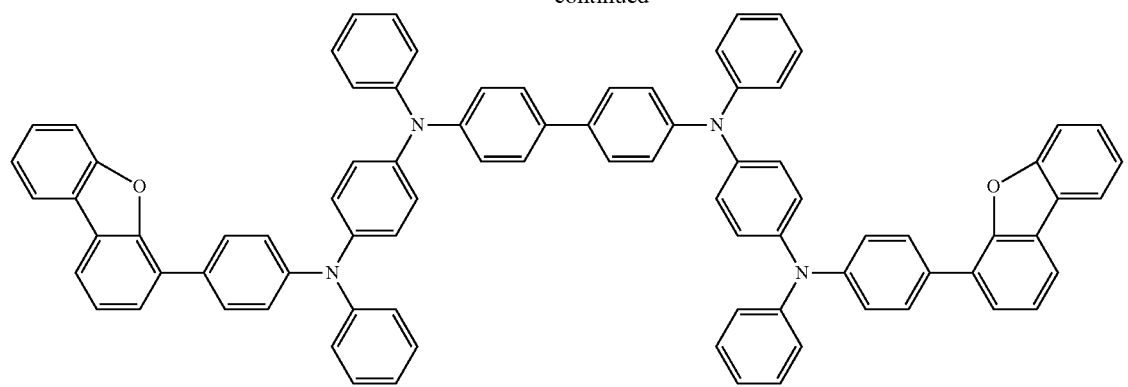
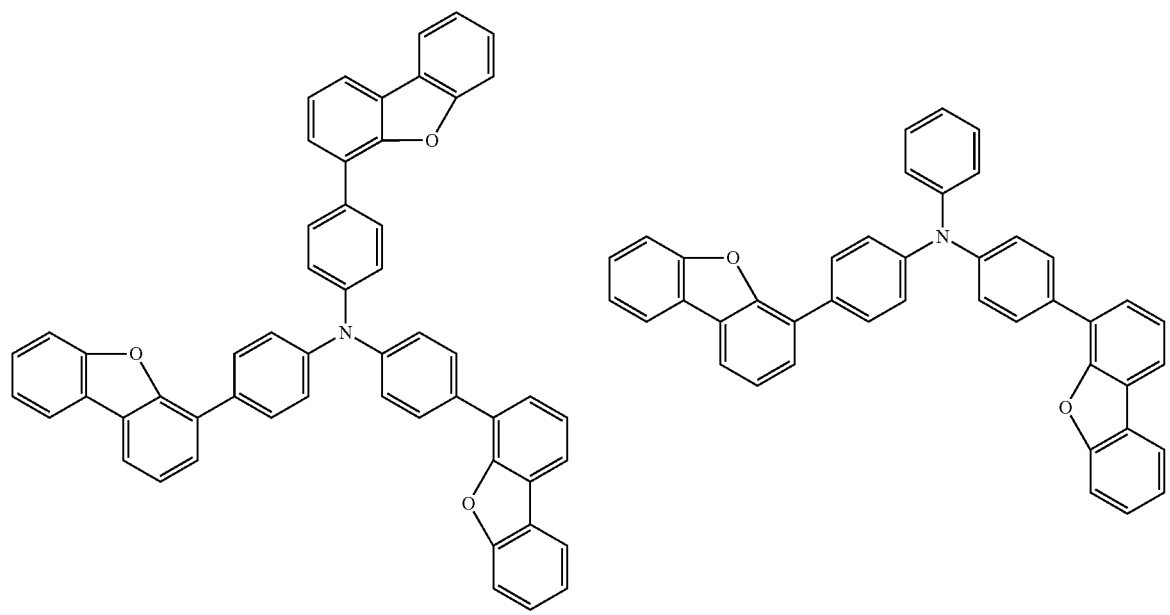
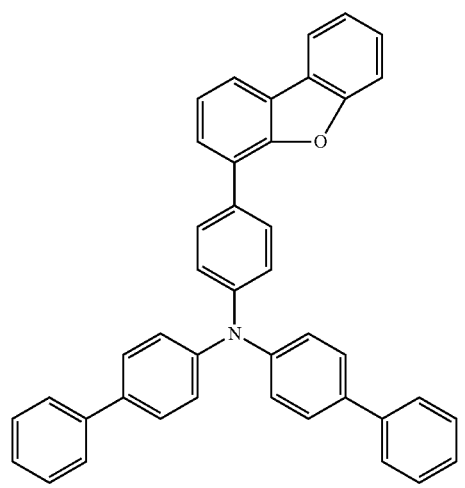

-continued
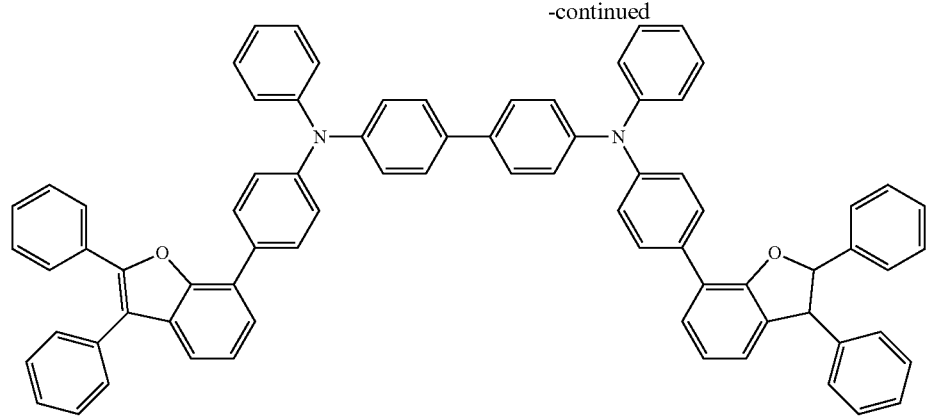
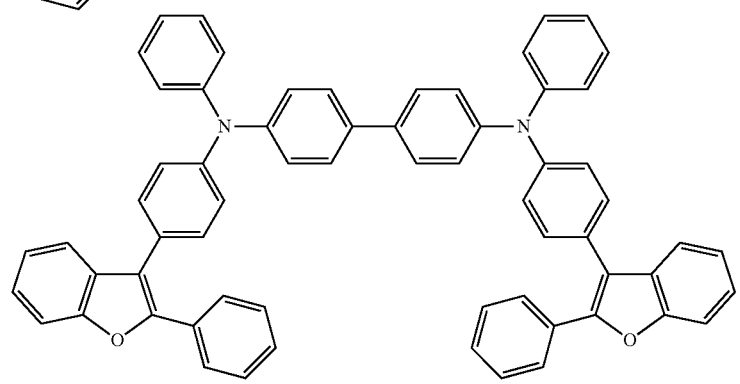
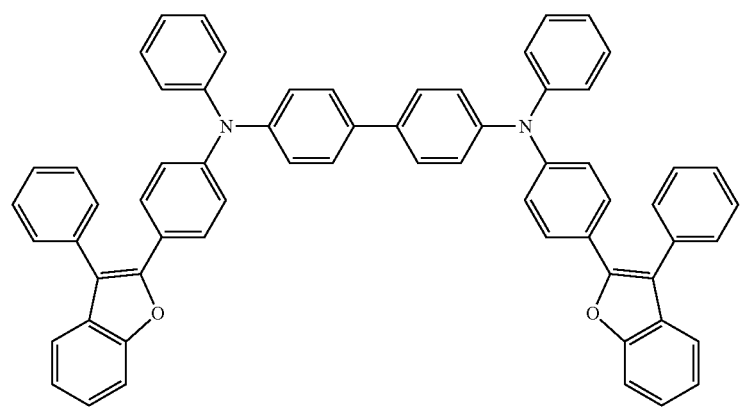
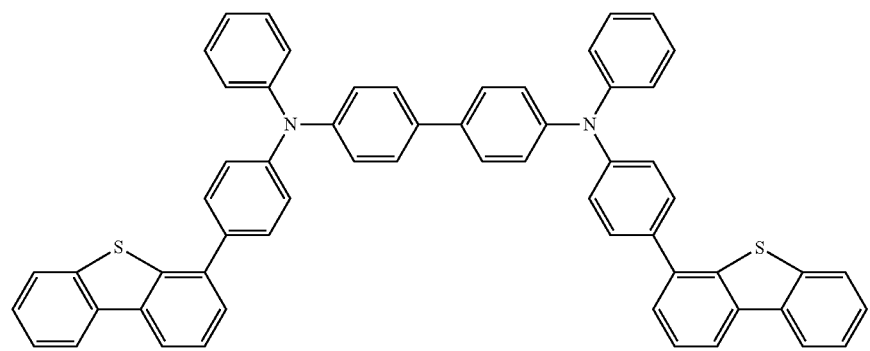

-continued
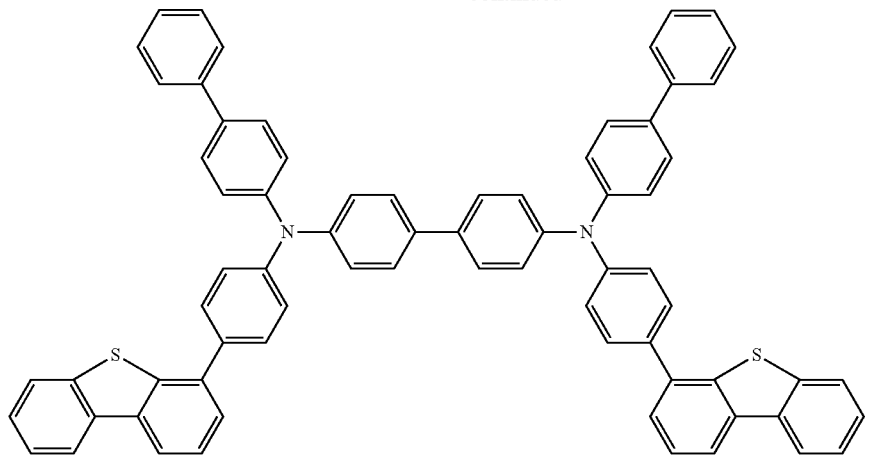
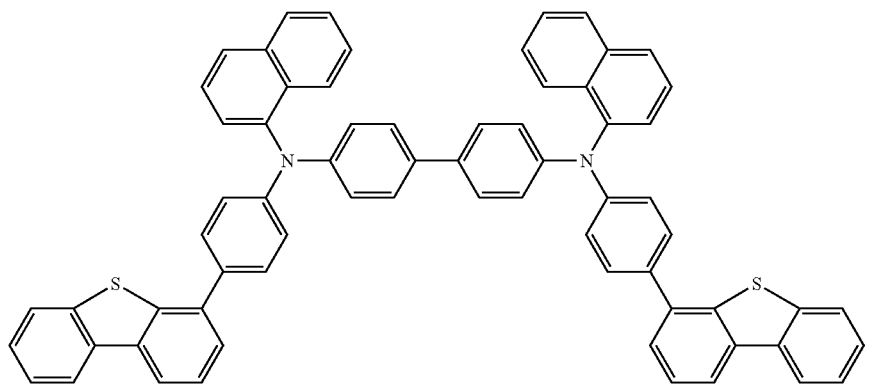
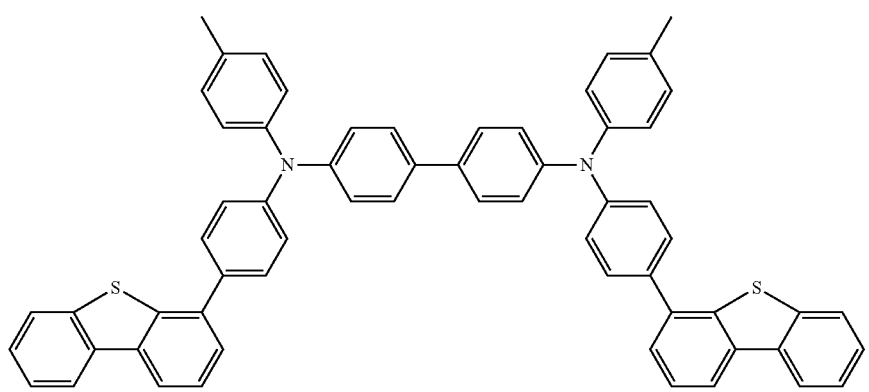
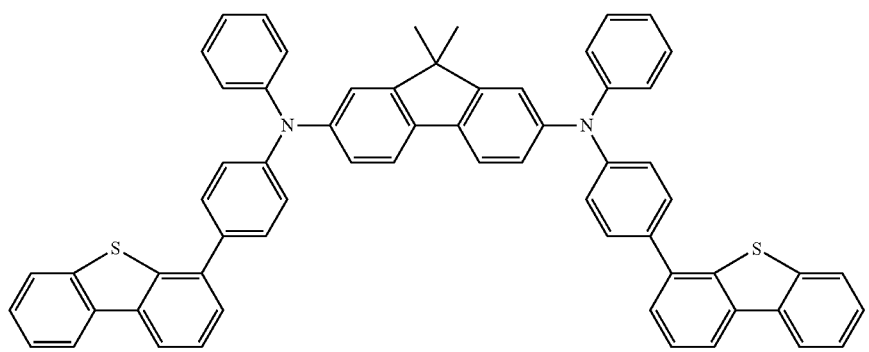

-continued
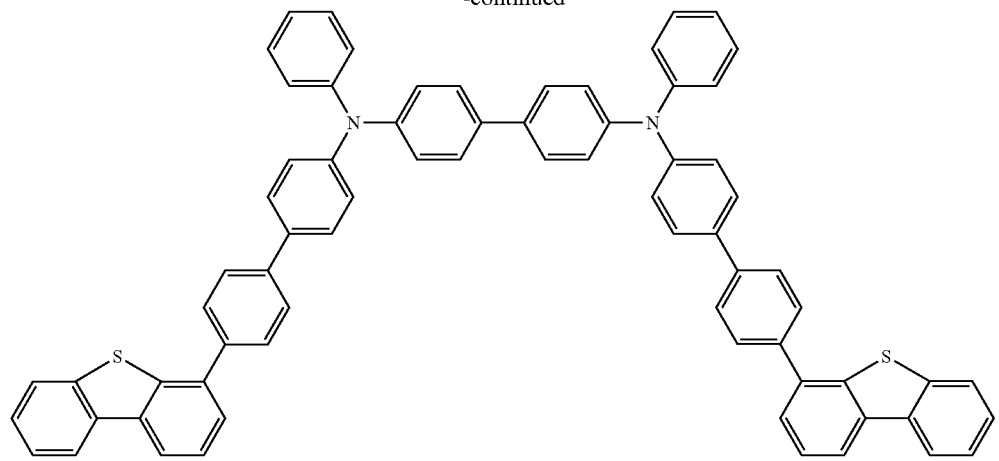
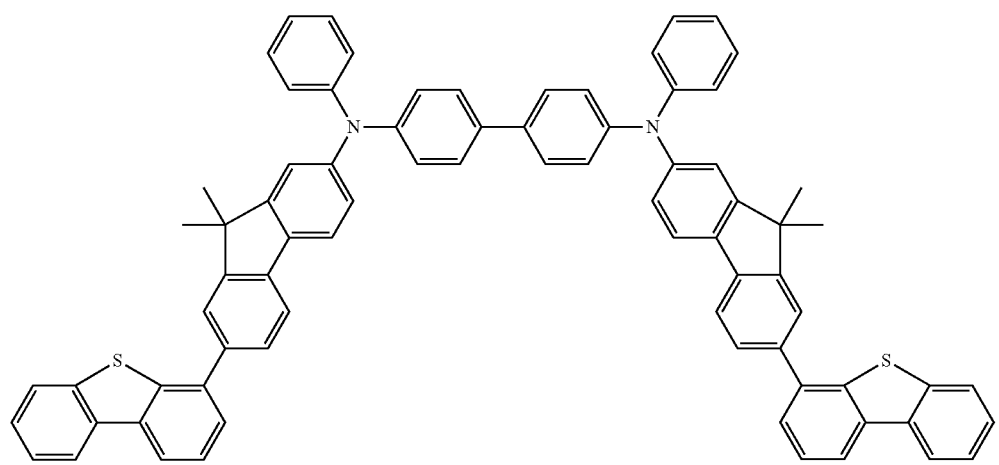
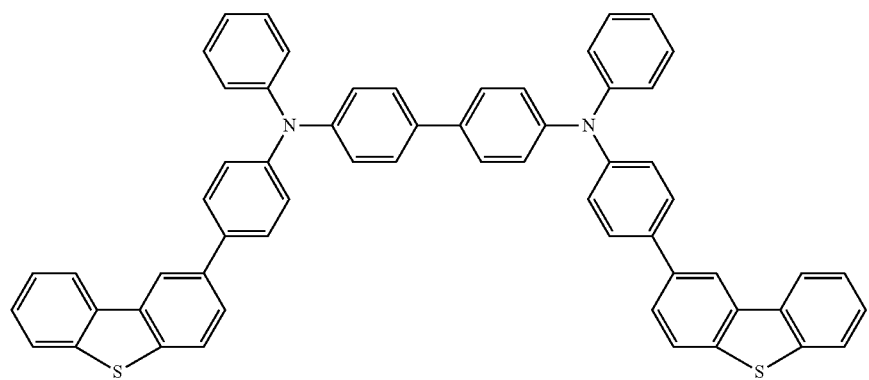

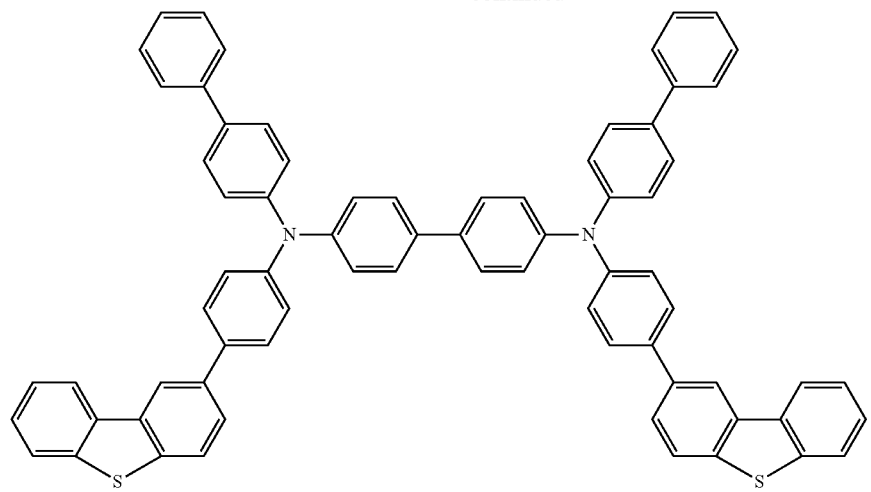
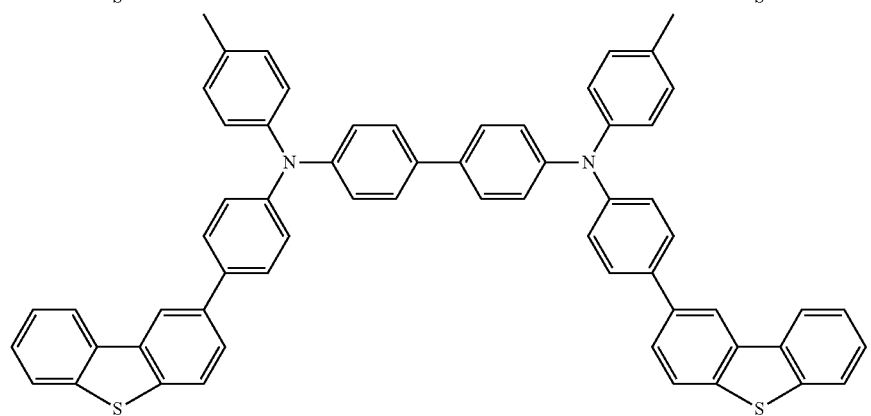
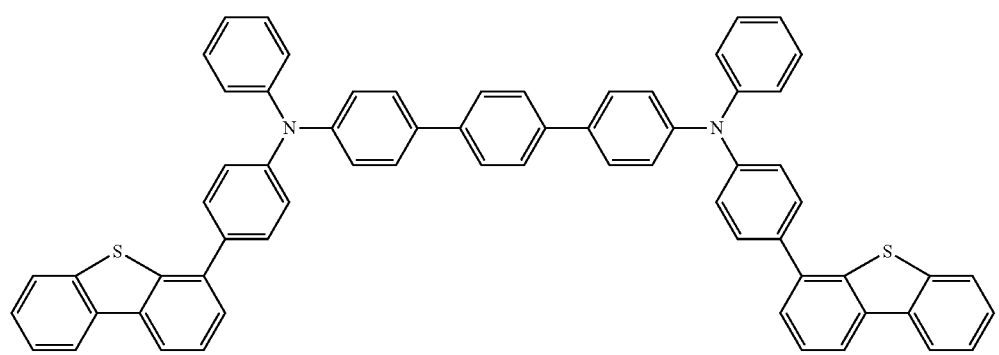
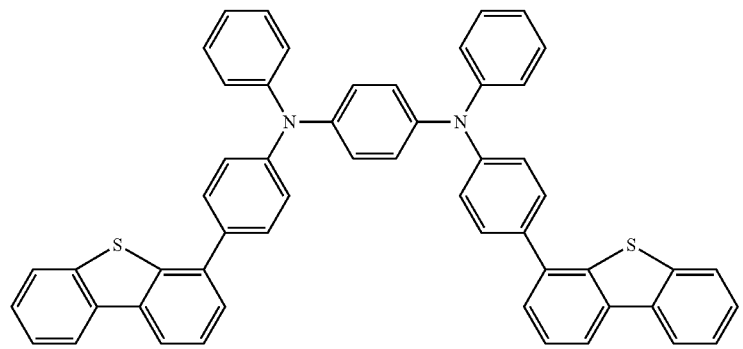

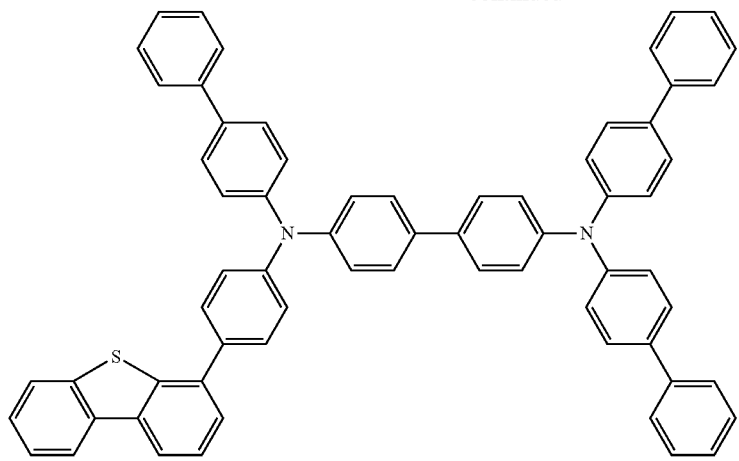
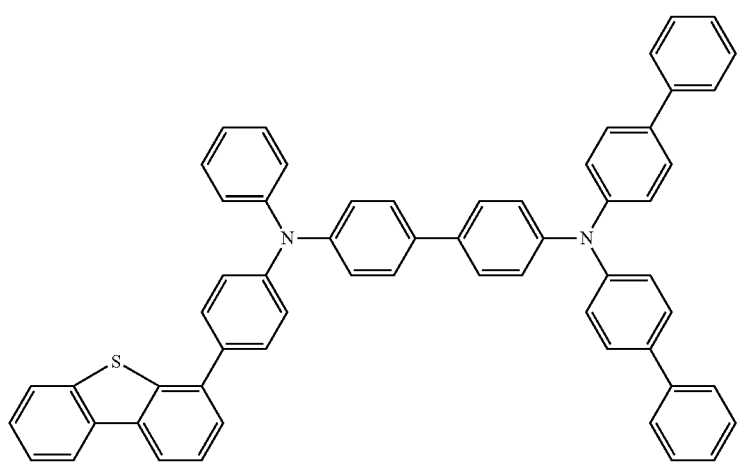
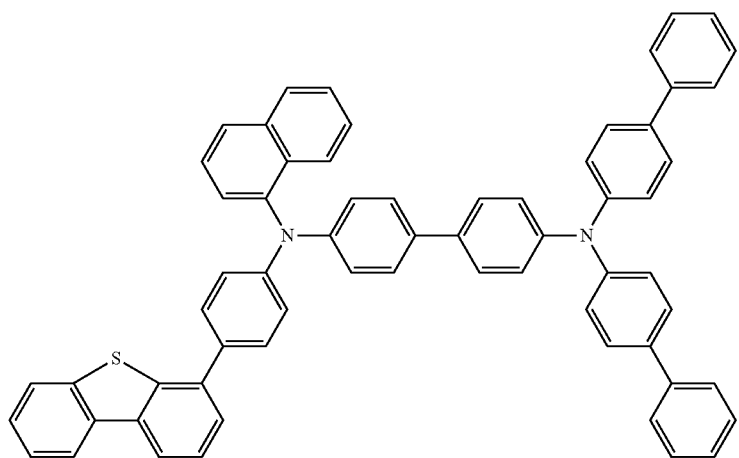

-continued
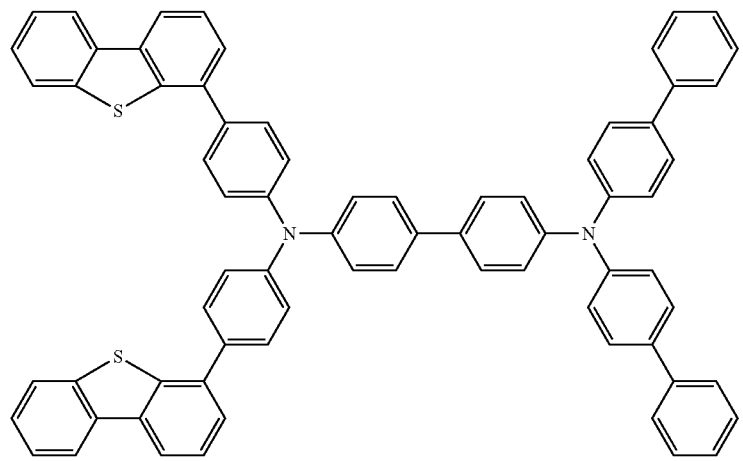
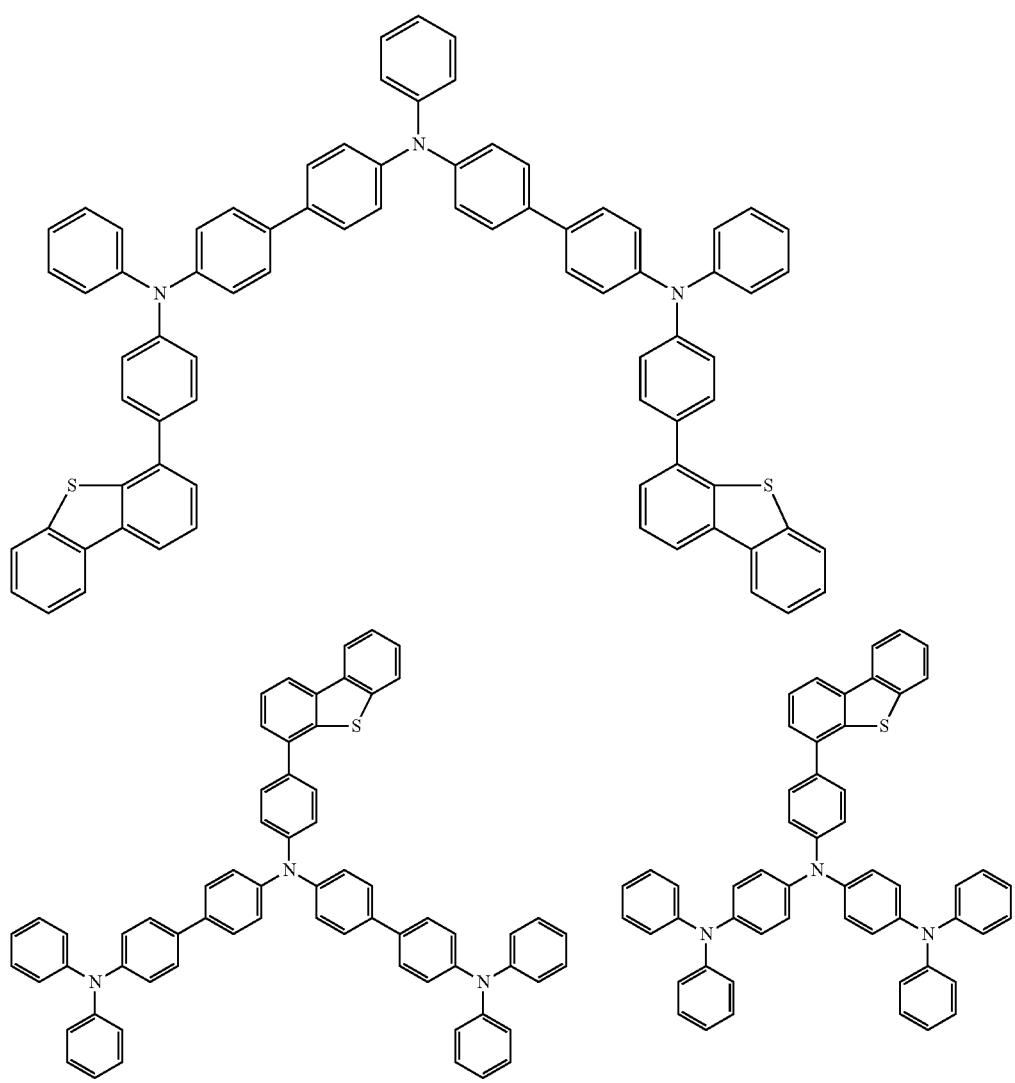

-continued
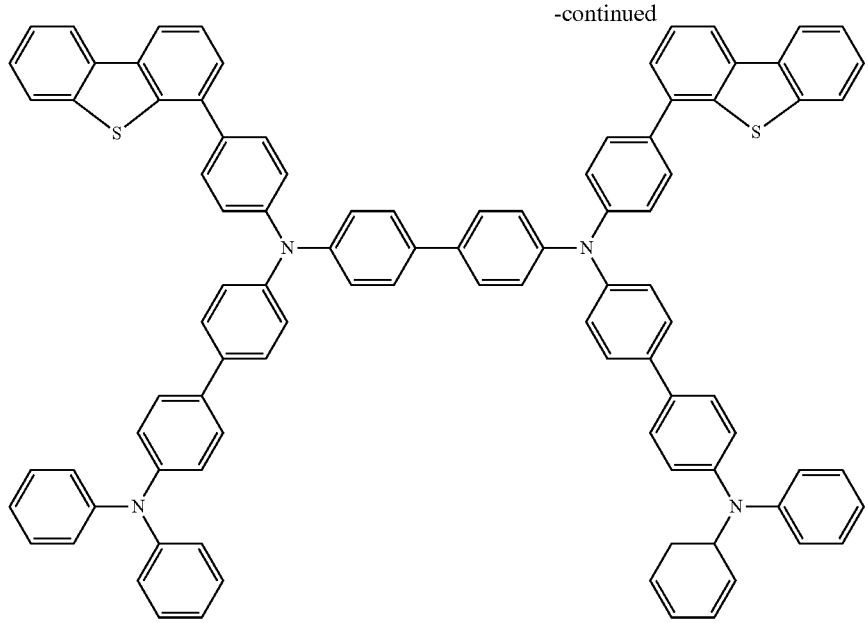
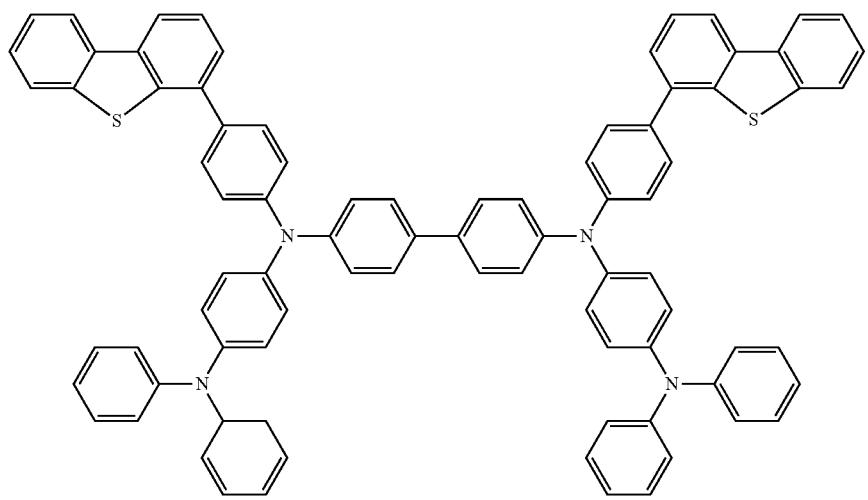
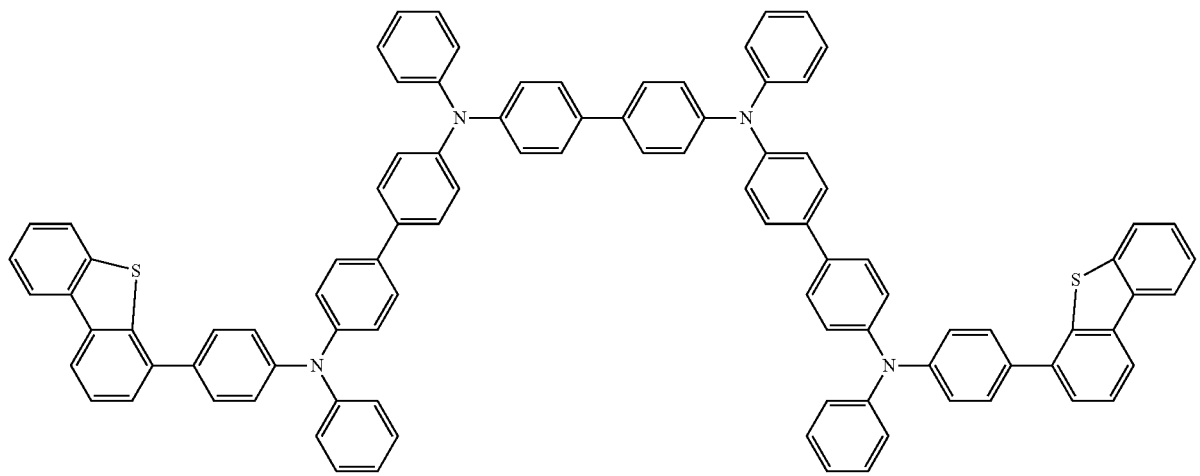

-continued
| 41 | 42 |
|---|---|
| 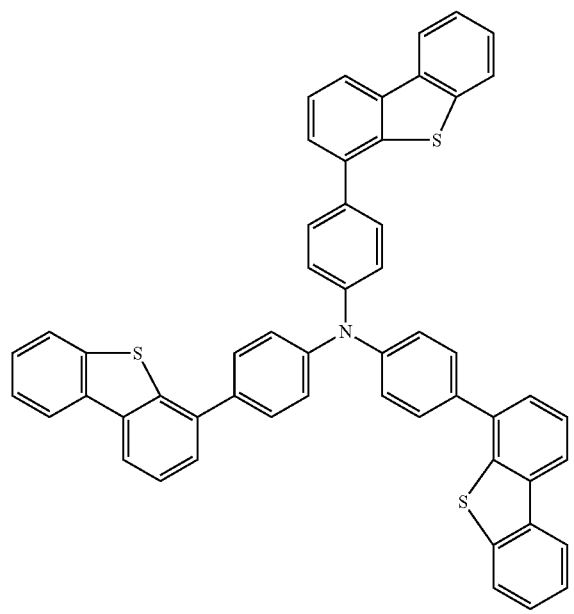 | 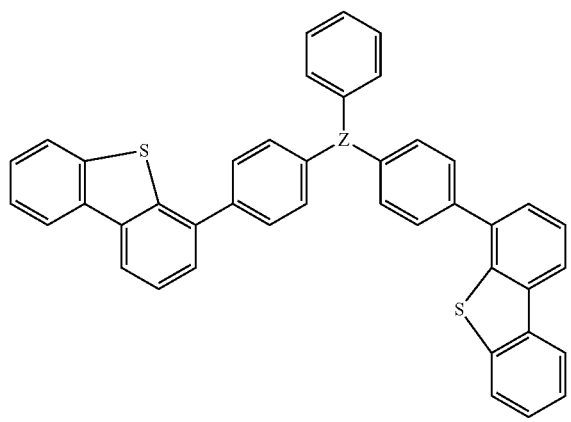 |
| 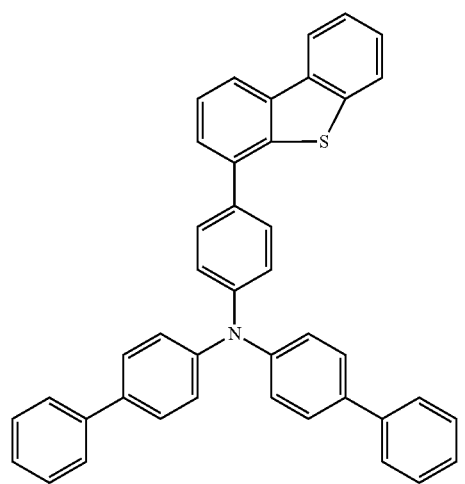 | 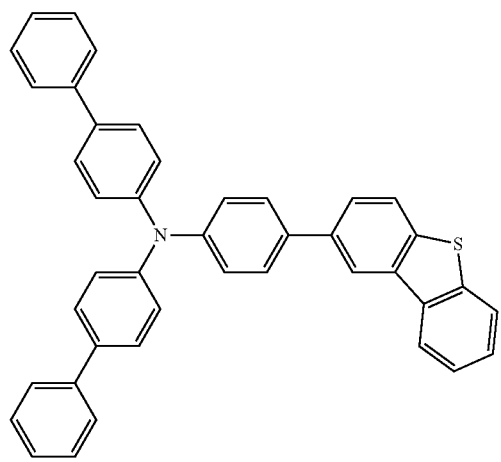 |
| 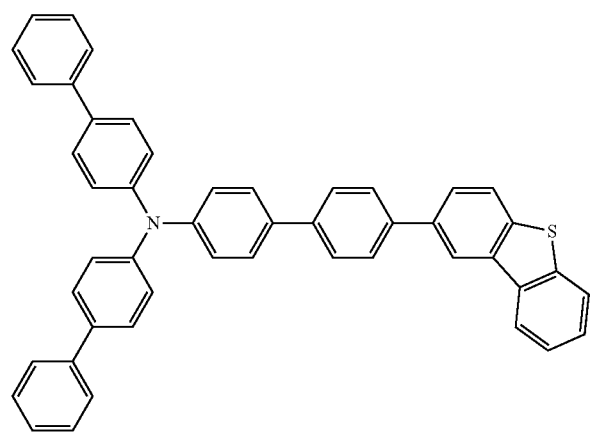 | 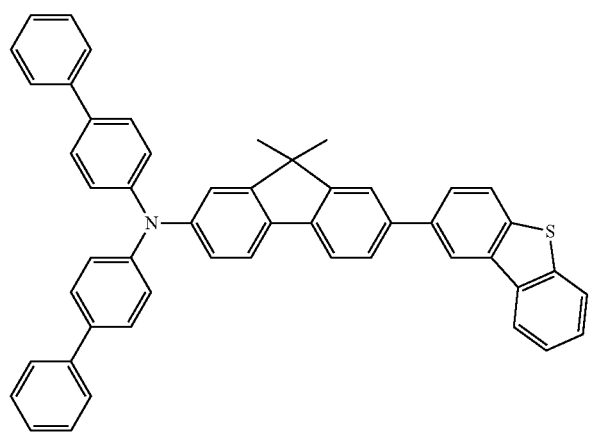 |

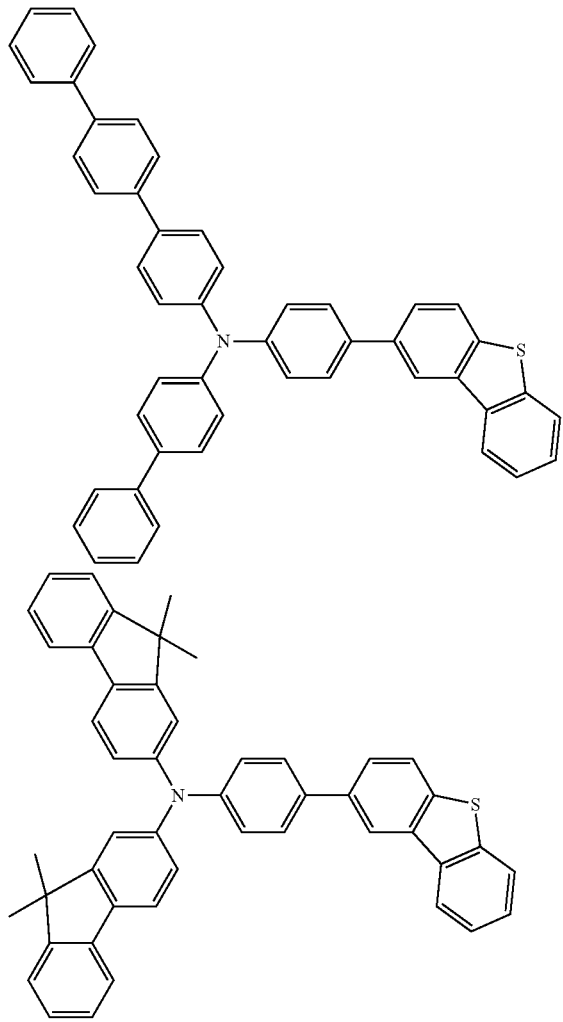
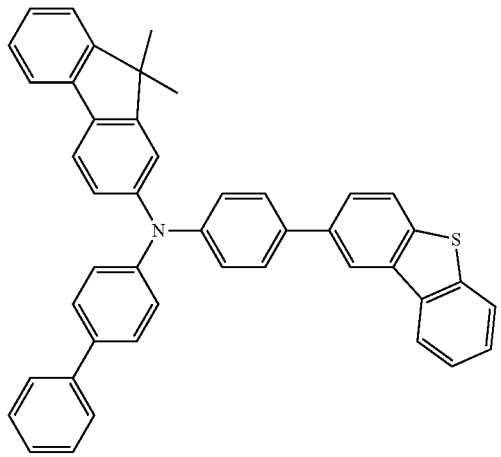

Next, the organic EL device of the present invention shall be explained.

In the organic EL device of the present invention in which an organic thin film layer comprising a single layer or plural layers including at least a light emitting layer is interposed between a cathode and an anode, at least one layer of the above organic thin film layer contains the aromatic amine derivative described above in the form of a single component or a mixed component.

In the organic EL device of the present invention, the organic thin film layer described above has a hole transporting layer, and the above hole transporting layer contains preferably the aromatic amine derivative of the present invention in the form of a single component or a mixed component. Further, the hole transporting layer described above contains more preferably the aromatic amine derivative of the present invention as a principal component.

The aromatic amine derivative of the present invention is used preferably for an organic EL device emitting light of a blue color base.

The organic electroluminescence device of the present invention contains preferably a styrylamine compound and/or an arylamine compound in a light emitting layer.

The arylamine compound includes a compound represented by the following Formula (1), and the styrylamine compound includes a compound represented by the following Formula (II):

(in Formula (1), $Ar_8$ is a group selected from phenyl, biphenyl, terphenyl, stilbene and distyrylaryl; $Ar_9$ and $Ar_{10}$ each are a hydrogen atom or an aromatic group having 6 to 20 carbon atoms, and $Ar_9$ and $Ar_{10}$ may be substituted; p' is an integer of 1 to 4; and $Ar_9$ and/or $Ar_{10}$ are more preferably substituted with a styryl group).

In this regard, the aromatic group having 6 to 20 carbon atoms includes preferably phenyl, naphthyl, anthranyl, phenanthryl, terphenyl and the like.

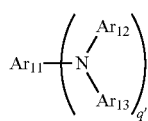

(in Formula (II), $Ar_{11}$ to $Ar_{13}$ are an aryl group having 5 to 40 ring carbon atoms which may be substituted, and is an integer of 1 to 4).

In this regard, the aryl group having 5 to 40 ring carbon atoms includes preferably phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acenaphthofluoranthenyl, stilbene and the like. The aryl group having 5 to 40 ring carbon atoms may further be substituted with a substituent, and the preferred substituent includes an alkyl group having 1 to 6 carbon atoms (ethyl, methyl, i-propyl, n-propyl, s-butyl, t-butyl, pentyl, hexyl, cyclopentyl, cyclohexyl and the like), an alkoxy group having 1 to 6 carbon atoms (ethoxy, methoxy, i-propoxy, n-propoxy, s-butoxy, t-butoxy, pentoxy, hexyloxy, cyclopentoxy, cyclohexyloxy and the like), an aryl group having 5 to 40 ring carbon atoms, an amino group substituted with an aryl group having 5 to 40 ring carbon atoms, an ester group having an aryl group having 5 to 40 ring carbon atoms, an ester group having an alkyl group having 1 to 6 carbon atoms, a cyano group, a nitro group and a halogen atom (chlorine, bromine, iodine and the like).

The device structure of the organic EL device of the present invention shall be explained below.

(1) Structure of the Organic EL Element

The typical examples of the device structure of the organic EL device of the present invention include structures such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/electron injecting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting layer/hole transporting layer/light emitting layer/insulating layer/cathode
(13) Anode/insulating layer/hole injecting layer/hole transporting layer/light emitting layer/electron injecting layer/cathode Among them, usually the structure of (8) is preferably used, but it shall not be restricted to them.

The aromatic amine derivative of the present invention may be used in any organic thin film layer of the organic EL device and can be used in the light emitting zone or the hole transporting zone, and it is used preferably in the hole transporting zone, particularly preferably in the hole transporting layer, whereby the molecules are less liable to be crystallized, and a yield in producing the organic EL device is elevated.

An amount of the aromatic amine derivative of the present invention which is added to the organic thin film layer is preferably 30 to 100 mole %.

(2) Light Transmitting Substrate

The organic EL device of the present invention is prepared on a light transmitting substrate. The light transmitting substrate referred to in this case is a substrate for supporting the organic EL device, and it is preferably a flat substrate in which light in a visible region of 400 to 700 nm has a transmission factor of 50% or more.

To be specific, it includes a glass plate, a polymer plate and the like. In particular, the glass plate includes soda lime glass, barium.cndot.strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like.

(3) Anode

An anode in the organic EL device of the present invention has a function to inject a hole into the hole transporting layer or the light emitting layer, and it is effective that the anode has a work function of 4.5 eV or more. The specific examples of a material for the anode used in the present invention include indium tin oxide alloy (ITO), zinc oxide (NESA), indium-zinc oxide (IZO), gold, silver, platinum, copper and the like.

The anode can be prepared by forming a thin film of the above electrode substances by a method such as a vapor deposition method, a sputtering method and the like.

When light emitted from the light emitting layer is taken out from the anode, a transmission factor of the anode based on light emitted is preferably larger than 10%. A sheet resistance of the anode is preferably several hundred Ω/□ or less. A film thickness of the anode is selected, though depending on the material, in a range of usually 10 nm to 1 μm, preferably 10 to 200 nm.

(4) Light Emitting Layer

The light emitting layer in the organic EL device has the following functions of (1) to (3) in combination.
(1) Injecting function: a function in which a hole can be injected from an anode or a hole injecting layer in applying an electric field and in which an electron can be injected from a cathode or an electron injecting layer.
(2) Transporting function: a function in which a charge injected (electron and hole) is transferred by virtue of a force of an electric field.
(3) Light emitting function: a function in which a field for recombination of an electron and a hole is provided and in which this is connected to light emission.

Provided that a difference between an easiness in injection of a hole and an easiness in injection of an electron may be present and that a difference may be present in a transporting ability shown by the mobilities of a hole and an electron, and any one of the charges is preferably transferred.

A publicly known method such as, for example, a vapor deposition method, a spin coating method, an LB method and the like can be applied as a method for forming the above light emitting layer. In particular, the light emitting layer is preferably a molecular deposit film. In this case, the molecular deposit film means a thin film formed by depositing a material compound staying in a gas phase state and a film formed by solidifying a material compound staying in a solution state or a liquid phase state, and the above molecular deposit film can usually be distinguished from a thin film formed by the LB method (molecular accumulation film) by a difference in an aggregation structure and a higher order structure and a functional difference originating in it.

Further, as disclosed in Japanese Patent Application Laid-Open No. 51781/1982, the light emitting layer can be formed as well by dissolving a binding agent such as a resin and the material compound in a solvent to prepare a solution and then coating the solution by a spin coating method and the like to form a thin film.

In the present invention, publicly known light emitting materials other than the light emitting material comprising the aromatic amine derivative of the present invention may be added, if necessary, to the light emitting layer as long as the object of the present invention is not damaged. Further, a light emitting layer containing a different publicly known light emitting material may be laminated on the light emitting layer containing the light emitting material comprising the aromatic amine derivative of the present invention.

A luminescent material or a doping material which can be used for the light emitting layer together with the aromatic amine compound of the present invention includes, for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bis-styryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, fluorescent coloring matters and the like. However, it shall not be restricted to them.

The host material which can be used for the light emitting layer together with the aromatic amine compound of the present invention is preferably compounds represented by the following Formulas (i) to (ix).

Asymmetric anthracene compound represented by the following Formula (1):

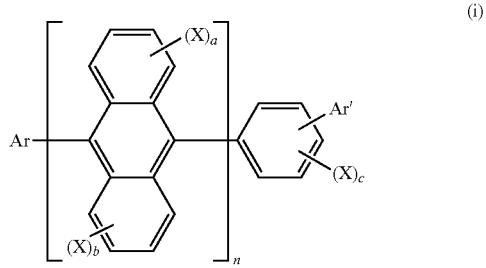

wherein Ar is a substituted or non-substituted fused aromatic group having 10 to 50 ring carbon atoms;
Ar' is a substituted or non-substituted aromatic group having 6 to 50 ring carbon atoms;
X is a substituted or non-substituted aromatic group having 6 to 50 ring carbon atoms, a substituted or non-substituted aromatic heterocyclic group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 ring carbon atoms, a carboxyl group, a halogen atom, a cyano group, a nitro group or a hydroxyl group;
a, b and c each are an integer of 0 to 4;
n is an integer of 1 to 3; and when n is 2 or more, an inside of brackets may be the same or different.

Asymmetric monoanthracene derivative represented by the following Formula (ii):

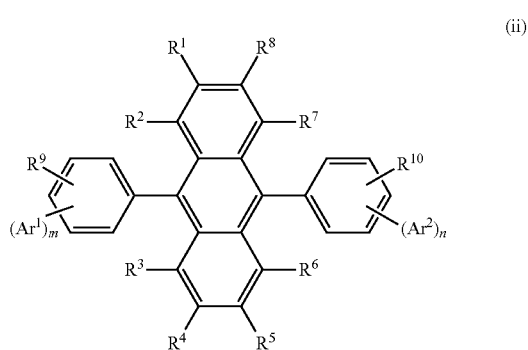

wherein $Ar^1$ and $Ar^2$ each are independently a substituted or non-substituted aromatic ring group having 6 to 50 ring carbon atoms; m and n each are an integer of 1 to 4; provided that when m and n are 1 and the positions of $Ar^1$ and $Ar^2$ bonded to the benzene ring are bilaterally symmetric, $Ar^1$ and $Ar^2$ are not the same, and when m and n are an integer of 2 to 4, m and n are different integers; and $R^1$ to $R^{10}$ each are independently a hydrogen atom, a substituted or non-substituted aromatic ring group having 6 to 50 ring carbon atoms, a substituted or non-substituted aromatic heterocyclic group having 5 to 50 ring carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 ring carbon atoms, a substituted or non-substituted silyl group, a carboxyl group, a halogen atom, a cyano group, a nitro group or a hydroxyl group.

Asymmetric pyrene derivative represented by the following Formula (iii):

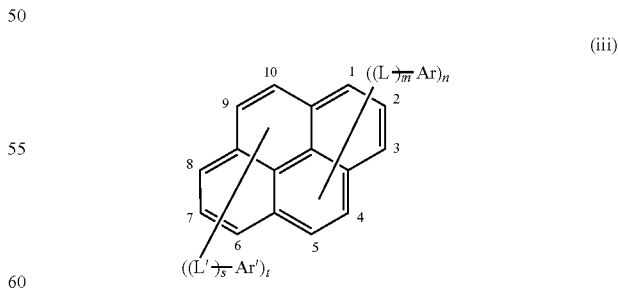

wherein Ar and Ar' each are a substituted or non-substituted aromatic group having 6 to 50 ring carbon atoms;
L and L' each are a substituted or non-substituted phenylene group, a substituted or non-substituted naphthalenylene group, a substituted or non-substituted fluorenylene group or a substituted or non-substituted dibenzosilolylene group;

m is an integer of 0 to 2; n is an integer of 1 to 4; s is an integer of 0 to 2; and t is an integer of 0 to 4;

L or Ar is bonded to any of 1- to 5-positions of pyrene, and L' or Ar' is bonded to any of 6- to 10-positions of pyrene;

provided that when n+t is an even number, Ar, Ar', L and L' satisfy (1) or (2) described below:

(1) Ar≠Ar' and/or L≠L' (in this case, ≠ shows that both are groups having different structures) and (2) when Ar=Ar' and L=L', (2-1) m≠s and/or n≠t or (2-2) when m=s and/or n=t, there are not a case in which (2-2-1) L and L' or pyrene each are bonded to different bonding positions on Ar and Ar' or (2-2-2) L and L' or pyrene are bonded to the same bonding position on Ar and Ar' and a case in which the substitution positions of L and L' or Ar and Ar' in pyrene are a 1-position and a 6-position or a 2-position and a 7-position.

Asymmetric anthracene derivative represented by the following Formula (Iv):

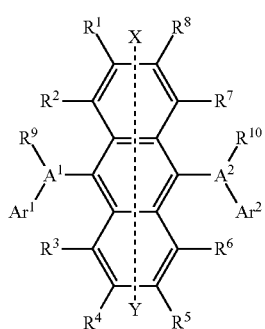

(iv)

wherein $A^1$ and $A^2$ each are independently a substituted or non-substituted fused aromatic group having 10 to 20 ring carbon atoms;

$Ar^1$ and $Ar^2$ each are independently a hydrogen atom or a substituted or non-substituted aromatic ring group having 6 to 50 ring carbon atoms;

$R^1$ to $R^{10}$ each are independently a hydrogen atom, a substituted or non-substituted aromatic ring group having 6 to 50 ring carbon ring atoms, a substituted or non-substituted aromatic heterocyclic group having 5 to 50 ring carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 ring carbon atoms, a substituted or non-substituted silyl group, a carboxyl group, a halogen atom, a cyano group, a nitro group or a hydroxyl group;

$Ar^1$, $Ar^2$, $R^9$ and $R^{10}$ each may be plural, and adjacent ones may form a saturated or unsaturated cyclic structure;

provided that there is no case in which in Formula (1), groups symmetric to an X-Y axis shown on the above anthracene are bonded to a 9-position and a 10-position of central anthracene.

Anthracene derivative represented by the following Formula (v):

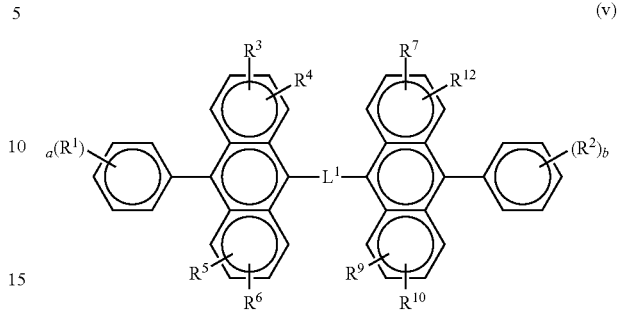

(v)

wherein $R^1$ to $R^{10}$ each represent independently a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; a and b each represent an integer of 1 to 5; when they are 2 or more, $R^1$'s themselves or $R^2$'s themselves each may be the same as or different from each other, and $R^1$'s themselves or $R^2$'s themselves may be combined with each other to form a ring; $R^3$ and $R^4$, $R^5$ and $R^6$, $R^7$ and $R^8$ and $R^9$ and $R^{10}$ may be combined with each other to form rings; and $L^1$ represents a single bond, —O—, —S—, —N(R)— (R is an alkyl group or an aryl group which may be substituted), an alkylene group or an arylene group.

Anthracene derivative represented by the following Formula (vi):

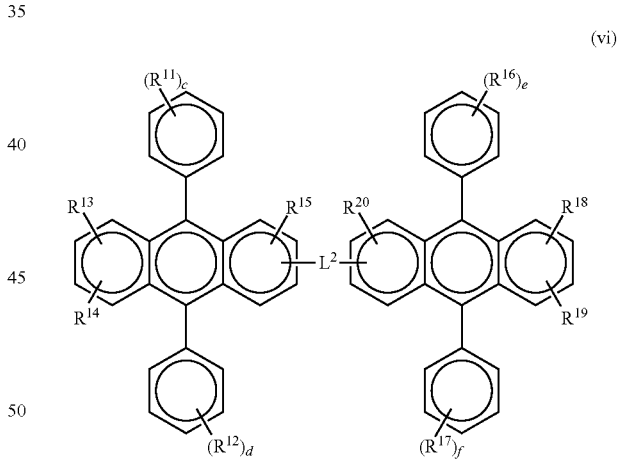

(vi)

wherein $R^{11}$ to $R^{20}$ each represent independently a hydrogen atom, an alkyl group, a cycloalkyl group, an aryl group, an alkoxyl group, an aryloxy group, an alkylamino group, an arylamino group or a heterocyclic group which may be substituted; c, d, e and f each represent an integer of 1 to 5; when they are 2 or more, $R^{11}$'s themselves, $R^{12}$'s themselves, $R^{16}$'s themselves or $R^{17}$'s themselves may be the same as or different from each other, and $R^{11}$'s themselves, $R^{12}$'s themselves, $R^{18}$'s themselves or $R^{17}$'s themselves may be combined with each other to form a ring; R'3 and $R^{14}$ and $R^{18}$ and $R^{19}$ may be combined with each other to form rings; and $L^2$ represents a single bond, —O—, —S—, —N(R)— (R is an alkyl group or an aryl group which may be substituted), an alkylene group or an arylene group.

Spirofluorene derivative represented by the following Formula (vii):

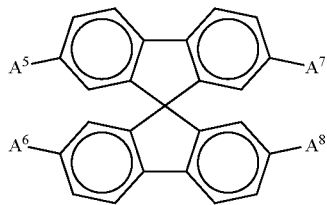

wherein $A^5$ to $A^8$ each are independently a substituted or non-substituted biphenyl group or a substituted or non-substituted naphthyl group.

Fused ring-containing compound represented by the following Formula (viii):

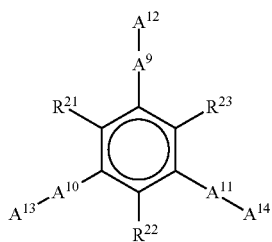

wherein $A^9$ to $A^{14}$ are the same as those described above; $R^{21}$ to $R^{23}$ each represent independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of $A^9$ to $A^{14}$ is a group having 3 or more fused aromatic rings.

Fluorene compound represented by the following Formula (ix):

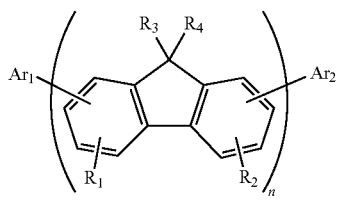

wherein $R_1$ and $R_2$ represent a hydrogen atom, a substituted or non-substituted alkyl group, a substituted or non-substituted aralkyl group, a substituted or non-substituted aryl group, a substituted or non-substituted heterocyclic group, a substituted amino group, a cyano group or a halogen atom; $R_1$'s themselves and $R_2$'s themselves which are bonded to the different fluorene groups may be the same as or different from each other, and $R_1$ and $R_2$ which are bonded to the same fluorene group may be the same as or different from each other; $R_3$ and $R_4$ represent a hydrogen atom, a substituted or non-substituted alkyl group, a substituted or non-substituted aralkyl group, a substituted or non-substituted aryl group or a substituted or non-substituted heterocyclic group; $R_3$'s themselves and $R_4$'s themselves which are bonded to the different fluorene groups may be the same as or different from each other, and $R_3$ and $R_4$ which are bonded to the same fluorene group may be the same as or different from each other; $Ar_1$ and $Ar_2$ represent a substituted or non-substituted fused polycyclic aromatic group in which the total of benzene rings is 3 or more or a fused polycyclic heterocyclic group in which the total of benzene rings and heterocycles is 3 or more or and which is bonded to the fluorene group via substituted or non-substituted carbon; $Ar_1$ and $Ar_2$ may be the same or different; and n represents an integer of 1 to 10.

Among the host materials described above, the anthracene derivatives are preferred, and the monoanthracene derivatives are more preferred. The asymmetric anthracene derivatives are particularly preferred.

Phosphorescent compounds can also be used as the luminescent material of a dopant. Compounds containing a carbazole ring for a host material are preferred as the phosphorescent compound. The dopant is a compound which can emit light from a triplet exciton, and it shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred.

The host suited to phosphorescence comprising the compound containing a carbazole ring is a compound having a function in which transfer of energy from an excited state thereof to a phosphorescent compound takes place to result in allowing the phosphorescent compound to emit light. The host compound shall not specifically be restricted as long as it is a compound which can transfer exciton energy to the phosphorescent compound, and it can suitably be selected according to the purposes. It may have an optional heterocycle in addition to a carbazole ring.

The specific examples of the above host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene base compounds, porphyrin base compounds, anthraquinonedimethane derivatives, anthrone derivatives, diphenylquinone derivatives, thiopyran dioxide derivatives, carbodiimide derivatives, fluorenilidenemethane derivatives, distyrylpyrazine derivatives, heterocyclic tetracarboxylic anhydride such as naphthaleneperylene, metal complexes of phthalocyanine derivatives and 8-quinolinol derivatives, various metal complex polysilane base compounds represented by metal complexes comprising metal phthalocyanine, benzoxazole and benzothiazole as ligands and macromolecule compounds including poly(N-vinylcarbazole) derivatives, aniline base copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination two or more kinds thereof.

The specific examples thereof include the following compounds:

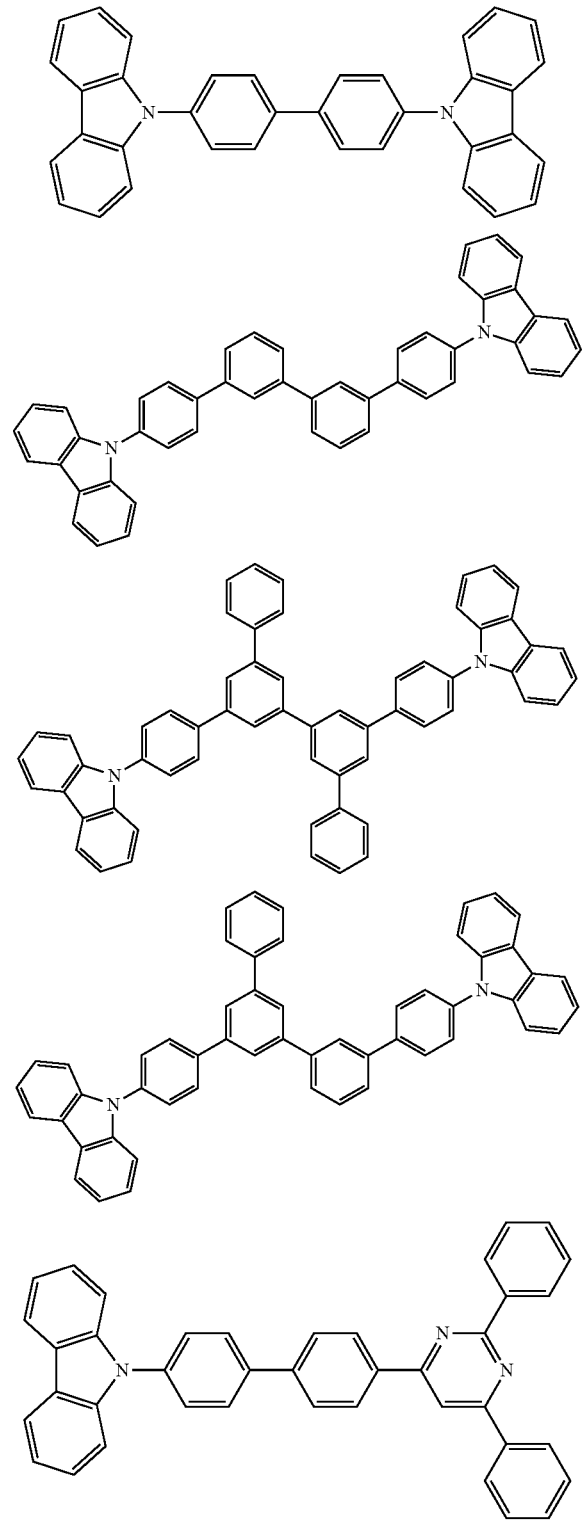

The phosphorescent dopant is a compound which can emit light from a triplet exciton. It shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred. The porphyrin metal complex is preferably a porphyrin platinum complex. The phosphorescent compounds may be used alone or in combination of two or more kinds thereof.

A ligand forming the ortho-metallated metal complex includes various ones, and the preferred ligand includes 2-phenylpyridine derivatives, 7,8-benzoquinoline derivatives, 2-(2-thienyl)pyridine derivatives, 2-(1-naphthyl)pyridine derivatives, 2-phenylquinoline derivatives and the like. The above derivatives may have, if necessary, substituents. In particular, the compounds into which fluorides and trifluoromethyl are introduced are preferred as a blue color dopant. Further, it may have, as an auxiliary ligand, ligands other than the ligands described above such as acetylacetonate, picric acid and the like.

A content of the phosphorescent dopant in the light emitting layer shall not specifically be restricted, and it can suitably be selected according to the purposes. It is, for example, 0.1 to 70 mass %, preferably 1 to 30 mass %. If a content of the phosphorescent dopant is less than 0.1 mass %, light emission is faint, and an addition effect thereof is not sufficiently exhibited. On the other hand, if it exceeds 70 mass %, a phenomenon called concentration quenching becomes marked, and the device performance is reduced.

The light emitting layer may contain, if necessary, a hole transporting material, an electron transporting material and a polymer binder.

Further, a film thickness of the light emitting layer is preferably 5 to 50 nm, more preferably 7 to 50 nm and most preferably 10 to 50 nm. If it is less than 5 nm, it is difficult to form the light emitting layer, and controlling of the chromaticity is likely to become difficult. On the other hand, if it exceeds 50 nm, the driving voltage is likely to go up.

(5) Hole Injecting and Transporting Layers (Hole Transporting Zone)

The hole injecting and transporting layers are layers for assisting injection of a hole into the light emitting layer to transport it to the light emitting region, and they have a large hole mobility and show a small ionization energy of usually 5.5 eV or less. A material which transports a hole to the light emitting layer by a lower electric field strength is preferred as the above hole injecting and transporting layers, and more preferred is a material in which a mobility of a hole is at least $10^{-4}$ cm$^2$/V·second in applying an electric field of, for example, $10^4$ to $10^6$ V/cm.

When the aromatic amine derivative of the present invention is used in the hole transporting zone, the hole injecting and transporting layers may be formed from the aromatic amine derivative of the present invention alone or it may be used in a mixture with other materials.

The materials for forming the hole injecting and transporting layers by mixing with the aromatic amine derivative of the present invention shall not specifically be restricted as long as they have the preferred properties described above, and capable of being used are optional materials selected from materials which have so far conventionally been used as charge transporting materials of holes in photoconductive materials and publicly known materials which are used for hole injecting and transporting layers in an organic EL device.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the like), polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto 10983/1976 and Japanese Patent Application Laid-Open No. 93224/1976, ditto 17105/1980, ditto 4148/1981, ditto 10866/1980, ditto 156953/1980 and ditto 36656/1981 and the like), pyrazoline derivatives and pyrazolone derivatives (refer to U.S. Pat. No. 3,180,729 and ditto U.S. Pat. No. 4,278,746 and Japanese Patent Application Laid-Open No. 88064/1980, ditto 88065/1980, ditto 105537/1974, ditto 51086/1980, ditto 80051/1981, ditto 88141/1981, ditto 45545/1982, ditto 112637/1979 and ditto 74546/1980 and the like), phenylenediamine derivatives (refer to U.S. Pat. No. 3,615,404, Japanese Patent Publication No. 10105/1976, ditto 3712/1971 and ditto 25336/1972 and Japanese Patent Application Laid-Open No. 53435/1979, ditto 110536/1979 and ditto 119925/1979 and the like), arylamine derivatives (refer to U.S. Pat. No. 3,567,450, ditto U.S. Pat. No. 3,180, 703, ditto U.S. Pat. No. 3,240,597, ditto U.S. Pat. No. 3,658, 520, ditto U.S. Pat. No. 4,232,103, ditto U.S. Pat. No. 4,175, 961 and ditto U.S. Pat. No. 4,012,376, Japanese Patent Publication No. 35702/1974 and ditto 27577/1964, Japanese Patent Application Laid-Open No. 144250/1980, ditto 119132/1981 and ditto 22437/1981 and German Patent 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto 52063/1980, ditto 52064/1980, ditto 46760/1980, ditto 85495/1980, ditto 11350/1982 and ditto 148749/1982, Japanese Patent Application Laid-Open No. 311591/1990 and the like), stilbene derivatives (Japanese Patent Application Laid-Open No. 210363/1986, ditto 228451/1986, ditto 14642/1986, ditto 72255/1986, ditto 47646/1987, ditto 36674/1987, ditto 10652/1987, ditto 30255/1987, ditto 93455/1985, ditto 94462/1985, ditto 174749/1985 and ditto 175052/1985 and the like), silazane derivatives (U.S. Pat. No. 4,950,950), polysilane base (Japanese Patent Application Laid-Open No. 204996/1990), aniline base copolymers (Japanese Patent Application Laid-Open No. 282263/1990) and electroconductive high molecular oligomers (particularly thiophene oligomers) disclosed in Japanese Patent Application Laid-Open No. 211399/1989.

The compounds described above can be used as the material for the hole injecting and transporting layers, and preferably used are porphyrin compounds (disclosed in Japanese Patent Application Laid-Open No. 2956965/1988 and the like), aromatic tertiary amine compounds and styrylamine compounds (refer to U.S. Pat. No. 4,127,412 and Japanese Patent Application Laid-Open No. 27033/1978, ditto 58445/1979, ditto 149634/1979, ditto 64299/1979, ditto 79450/1980, ditto 144250/1980, ditto 119132/1981, ditto 295558/1986, ditto 98353/1986 and ditto 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4"-tris(N-(3-methylphenyl)-N-phenylamino)triphenylamine (hereinafter abbreviated as MTDATA) in which three triphenylamine units are combined in the form of a star burst type disclosed in Japanese Patent Application Laid-Open No. 308688/1992.

Further, inorganic compounds such as p type Si, p type SiC and the like can also be used as the material for the hole injecting and transporting layers in addition to the aromatic dimethylidene base compounds described above shown as the material for the light emitting layer.

In addition to the above compounds, a nitrogen-containing heterocyclic derivative represented by the following formula which is disclosed in Japanese Patent No. 3571977 can be used as well:

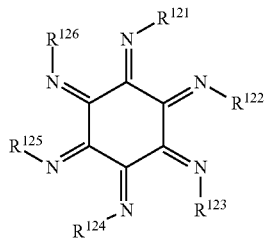

wherein $R^{121}$ to $R^{126}$ each represent any of a substituted or non-substituted alkyl group, a substituted or non-substituted aryl group, a substituted or non-substituted aralkyl group and a substituted or non-substituted heterocyclic group; provided that $R^{121}$ to $R^{126}$ may be the same or different; $R^{121}$ and $R^{122}$, $R^{122}$ and $R^{123}$, $R^{123}$ and $R^{124}$, $R^{124}$ and $R^{125}$, $R^{125}$ and $R^{126}$ and $R^{126}$ and $R^{121}$ may form fused rings.

Further, a compound represented by the following formula which is described in U.S. 2004/0113547 A1 can be used as well:

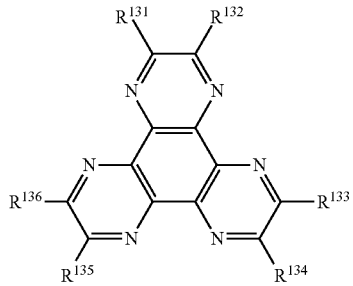

wherein R131 to R136 are substituents and are preferably electron attractive groups such as a cyano group, a nitro group, a sulfonyl group, a carbonyl group, a trifluoromethyl group, halogen atoms and the like.

As represented by the above materials, acceptor materials can also be used as the hole injecting material. The specific examples thereof have been described above.

Further, inorganic compounds such as p type Si, p type SiC and the like can also be used as the material for the hole injecting layer in addition to the aromatic dimethylidene base compounds described above shown as the material for the light emitting layer.

The hole injecting and transporting layers can be formed by making a thin film from the aromatic amine derivative of the present invention by a publicly known method such as, for example, a vacuum vapor deposition method, a spin coating method, a casting method, an LB method and the like. A film thickness of the hole injecting and transporting layers shall not specifically be restricted, and it is usually 5 nm to 5 The above hole injecting and transporting layers may be constituted from a single layer comprising at least one of the materials described above as long as the aromatic amine derivative of the present invention is contained in the hole transporting zone, and hole injecting and transporting layers comprising compounds which are different from those used in the hole injecting and transporting layers described above may be laminated thereon.

Further, an organic semiconductor layer may be provided as a layer for assisting injection of a hole or injection of an electron into the light emitting layer, and the layer having a conductance of $10^{-10}$ S/cm or more is suited. Capable of being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

(6) Electron Injecting and Transporting Layers

The electron injecting and transporting layers are layers for assisting injection of an electron into the light emitting layer to transport it to the light emitting region, and they have a large electron mobility. Also, the adhesion improving layer is a layer comprising particularly a material having a good adhesive property with the cathode in the above electron injecting layer.

It is known that since light emitted in an organic EL device is reflected by an electrode (in this case, a cathode), light transmitted directly from an anode is interfered with light emitted via reflection by the electrode. In order to make efficient use of the above interference effect, the electron transporting layer is suitably selected in a film thickness of several nm to several µm, and particularly when the film thickness is large, the electron mobility is preferably at least $10^{-5}$ cm$^2$/Vs or more in applying an electric field of $10^4$ to $10^6$ V/cm in order to avoid a rise in voltage.

The materials used for the electron injecting layer are suitably metal complexes of 8-hyroxyquinoline or derivatives thereof and oxadiazole derivatives. The specific examples of the metal complexes of 8-hyroxyquinoline or the derivatives thereof include metal chelate oxynoid compounds containing chelates of oxine (in general, 8-quinolinol or 8-hyroxyquinoline), and, for example, tris(8-quinolinol)aluminum can be used as the electron injecting material.

On the other hand, the oxadiazole derivative includes electron transmitting compounds represented by the following formulas:

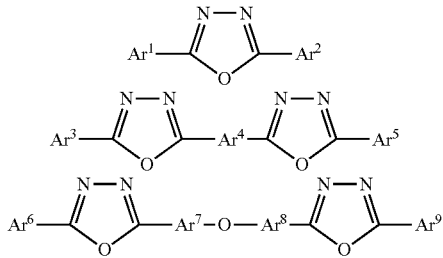

wherein Ar$^1$, Ar$^2$, Ar$^3$, Ar$^5$, Ar$^6$ and Ar$^9$ each represent a substituted or non-substituted aryl group, and they may be the same as or different from each other; Ar$^4$, Ar$^7$ and Ar$^8$ each represent a substituted or non-substituted arylene group, and they may be the same as or different from each other.

In this connection, the aryl group includes, for example, phenyl, biphenyl, anthranyl, perylenyl and pyrenyl. Also, the arylene group includes phenylene, naphthylene, biphenylene, anthranylene, perylenylene and pyrenylene. Substituents thereof include an alkyl group having 1 to 10 carbon atoms, an alkoxy group having 1 to 10 carbon atoms and a cyano group. The above electron transmitting compounds have preferably a thin film-forming property.

The following compounds can be given as the specific examples of the electron transmitting compounds described above:

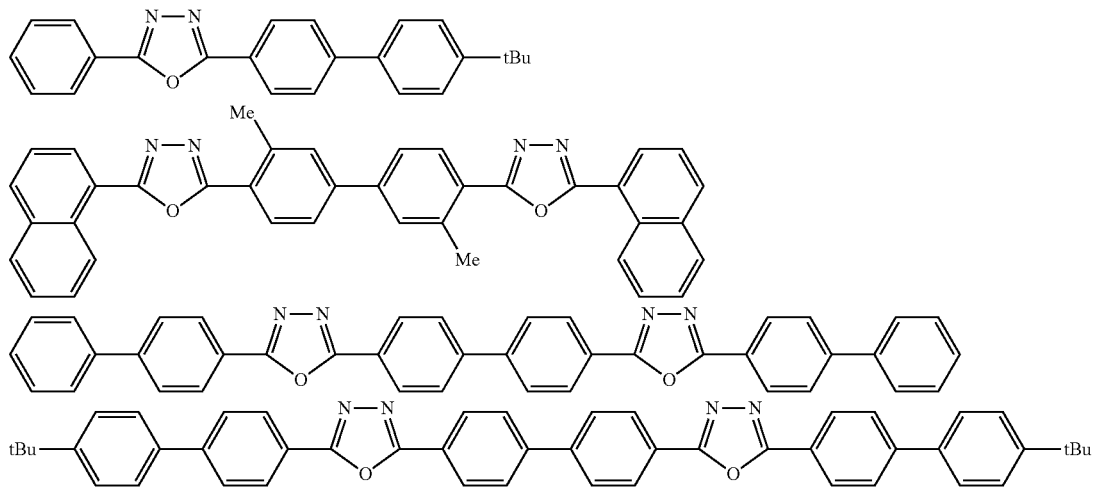

-continued

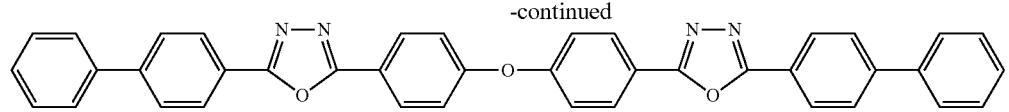

Further, Compounds represented by the following Formulas (A) to (F) can be used as the materials used for the electron injecting layer and the electron transporting layer.

Nitrogen-containing heterocyclic derivatives represented by:

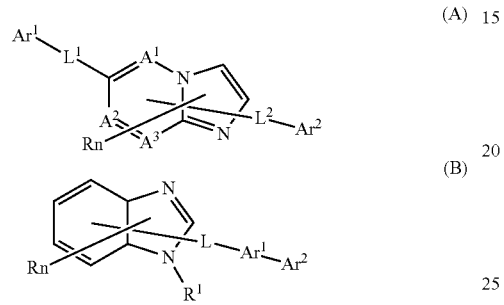

(A)

(B)

(in Formulas (A) and (B), $A^1$ to $A^3$ each are independently a nitrogen atom or a carbon atom; $Ar^1$ is a substituted or non-substituted aryl group having 6 to 60 ring carbon atoms or a substituted or non-substituted heteroaryl group having 3 to 60 ring carbon atoms; $Ar^2$ is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms or a divalent group thereof;

provided that any one of $Ar^1$ and $Ar^2$ is a substituted or non-substituted fused ring group having 10 to 60 ring carbon atoms or a substituted or non-substituted monohetero fused ring group having 3 to 60 ring carbon atoms;

$L_1$, $L_2$ and L each are independently a single bond, a substituted or non-substituted arylene group having 6 to 60 ring carbon atoms, a substituted or non-substituted heteroarylene group having 3 to 60 ring carbon atoms or a substituted or non-substituted fluorenylene group; R is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms; n is an integer of 0 to 5; when n is 2 or more, plural R's may be the same or different, and adjacent plural R's may be combined with each other to form a carbocyclic aliphatic ring or a carbocyclic aromatic ring).

Nitrogen-containing heterocyclic derivative represented by:

(C)

(wherein HAr is a nitrogen-containing heterocycle having 3 to 40 carbon atoms which may have a substituent; L is a single bond, an arylene group having 6 to 60 carbon atoms which may have a substituent, a heteroarylene group having 3 to 60 carbon atoms which may have a substituent or a fluorenylene group which may have a substituent; $Ar^1$ is a divalent aromatic hydrocarbon group having 6 to 60 carbon atoms which may have a substituent; and $Ar^2$ is an aryl group having 6 to 60 carbon atoms which may have a substituent or a heteroaryl group having 3 to 60 carbon atoms which may have a substituent).

Silacyclopentadiene derivative represented by:

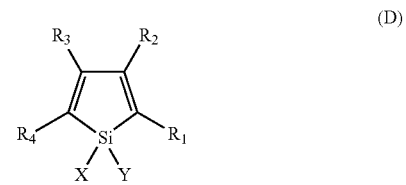

(D)

(wherein X and Y each are independently a saturated or unsaturated hydrocarbon group having 1 to 6 carbon atoms, an alkoxy group, an alkenyloxy group, an alkynyloxy group, a hydroxy group, a substituted or non-substituted aryl group, a substituted or non-substituted heterocycle or a structure in which X is combined with Y to form a saturated or unsaturated ring; $R^1$ to $R^4$ each are independently a hydrogen atom, a halogen atom, a substituted or non-substituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, a cyano group or a structure in which substituted or non-substituted rings are fused when they are adjacent).

Borane derivative represented by:

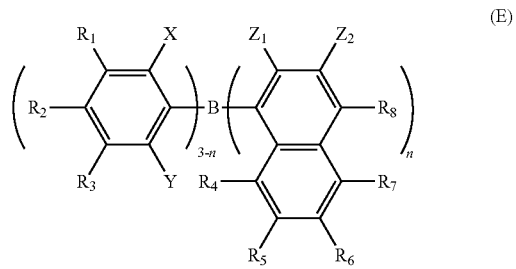

(E)

(wherein $R_1$ to $R_8$ and $Z_2$ each represent independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ each represent independently a saturated or unsaturated hydrocarbon group, an aromatic group, a heterocyclic group, a substituted amino group, an alkoxy group or an aryloxy group; substituents of $Z_1$ and $Z_2$ may be combined with each other to form a fused ring; n represents an integer of 1 to 3, and when n is 2 or more, $Z_1$'s may be different; provided that a case in which n is 1 and X, Y and $R_2$ are methyl and in which $R_8$ is a hydrogen atom or a substituted boryl group and a case in which n is 3 and $Z_1$ is methyl are not included).

(F)

[wherein $Q^1$ and $Q^2$ each represent independently a ligand represented by the following Formula (G), and L represents a halogen atom, a substituted or non-substituted alkyl group, a substituted or non-substituted cycloalkyl group, a substituted or non-substituted aryl group, a substituted or non-substituted heterocyclic group, —$OR^1$ ($R^1$ is a hydrogen atom, a substituted or non-substituted alkyl group, a substituted or non-substituted cycloalkyl group, a substituted or non-substituted aryl group or a substituted or non-substituted heterocyclic group) or a ligand represented by —O—Ga-$Q^3(Q^4)$ ($Q^3$ and $Q^4$ are the same as $Q^1$ and $Q^2$)]:

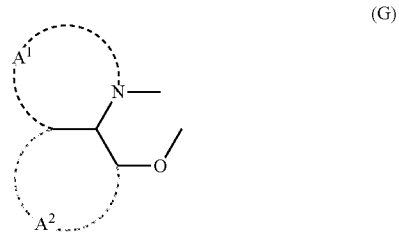

(G)

[wherein rings $A^1$ and $A^2$ are a six-membered aryl ring structure which may have a substituent and in which they are fused with each other].

The above metal complex has a strong property of an n type semiconductor and a large electron injecting ability. Further, since it has low production energy in forming the complex, a bonding property between the metal and the ligand in the metal complex formed becomes firm, and a fluorescence quantum efficiency of the luminescent material grows larger as well.

The specific examples of substituents of the rings A' and $A^2$ forming the ligand represented by Formula (G) include a halogen atom such as chlorine, bromine, iodine and fluorine, a substituted or non-substituted alkyl group such as methyl, ethyl, propyl, butyl, s-butyl, t-butyl, pentyl, hexyl, heptyl, octyl, stearyl, trichloromethyl and the like, a substituted or non-substituted aryl group such as phenyl, naphthyl, 3-methylphenyl, 3-methoxyphenyl, 3-fluorophenyl, 3-trichloromethylphenyl, 3-trifluoromethylphenyl, 3-nitrophenyl and the like, a substituted or non-substituted alkoxy group such as methoxy, n-butoxy, t-butoxy, trichloromethoxy, trifluoroethoxy, pentafluoropropoxy, 2,2,3,3-tetrafluoropropoxy, 1,1,3,3,3-hexafluoro-2-propoxy, 6-(perfluoroethyl)hexyloxy and the like, a substituted or non-substituted aryloxy group such as phenoxy, p-nitrophenoxy, p-t-butylphenoxy, 3-fluorophenoxy, pentafluorophenoxy, 3-trifluoromethylphenoxy and the like, a substituted or non-substituted alkylthio group such as methylthio, ethylthio, t-butylthio, hexylthio, octylthio trifluoromethylthio and the like, a substituted or non-substituted arylthio group such as phenylthio, p-nitrophenylthio, p-t-butylphenylthio, 3-fluorophenylthio, pentafluorophenylthio, 3-trifluoromethylphenylthio and the like, a cyano group, a nitro group, an amino group, a mono- or disubstituted amino group such as methylamino, diethylamino, ethylamino, diethylamino, dipropylamino, dibutylamino, diphenylamino and the like, an acylamino group such as bis(acetoxymethyl)amino, bis(acetoxyethyl)amino, bis(acetoxypropyl)amino, bis(acetoxybutyl)amino and the like, a hydroxy group, a siloxy group, an acyl group, a carbamoyl group such as methylcarbamoyl, dimethylcarbamoyl, ethylcarbamoyl, diethylcarbamoyl, propylcarbamoyl, butylcarbamoyl, phenylcarbamoyl and the like, a carboxylic acid group, a sulfonic acid group, an imide group, a cycloalkyl group such as cyclopentane, cyclohexyl and the like, an aryl group such as phenyl, naphthyl, biphenyl, anthranyl, phenanthryl, fluorenyl, pyrenyl and the like and a heterocyclic group such as pyridinyl, pyrazinyl, pyrimidinyl, pyridazinyl, triazinyl, indolinyl, quinolinyl, acridinyl, pyrrolidinyl, dioxanyl, piperidinyl, morpholidinyl, piperazinyl, triatinyl, carbazolyl, furanyl, thiophenyl, oxazolyl, oxadiazolyl, benzoxazolyl, thiazolyl, thiadiazolyl, benzothiazolyl, triazolyl, imidazolyl, benzimidazolyl, puranyl and the like. Further, the substituents described above may be combined with each other to form six-membered aryl rings or heterocycles.

The preferred mode of the organic EL device of the present invention includes a device containing a reducing dopant in the region which transports an electron or an interfacial region between the cathode and the organic layer. In this case, the reducing dopant is defined by a substance which can reduce an electron transporting compound. Accordingly, various compounds can be used as long as they have a reducing property of some extent, and capable of being suitably used is at least one substance selected from the group consisting of, for example, alkali metals, alkaline earth metals, rare earth metals, oxides of alkali metals, halides of alkali metals, oxides of alkaline earth metals, halides of alkaline earth metals, oxides of rare earth metals or halides of rare earth metals, organic complexes of alkali metals, organic complexes of alkaline earth metals and organic complexes of rare earth metals.

To be more specific, the preferred reducing dopant includes at least one alkali metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, the more preferred reducing dopant is at least one alkali metal selected from the group consisting of K, Rb and Cs, and it is more preferably Rb or Cs. It is most preferably Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example, Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

In the present invention, an electron injecting layer constituted from an insulator and a semiconductor may further be provided between the cathode and the organic layer. In this case, an electric current can effectively be prevented from leaking to enhance the electron injecting property. Preferably used as the above insulator is at least one metal compound selected from the group consisting of alkali metal chalcogenides, alkaline earth metal chalcogenides, halides of alkali metals and halides of alkaline earth metals. If the electron injecting layer is constituted from the above alkali metal chalcogenides, it is preferred from the viewpoint that the electron injecting property can further be enhanced. To be specific, the preferred alkali metal chalcogenides include, for example, $Li_2O$, $K_2O$, $Na_2S$, $Na_2Se$ and $Na_2O$, and the preferred alkaline earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkaline earth metals include, for example, fluorides such as $CaF_2$, $BaF_2$, $SrF_2$, $MgF_2$ and $BeF_2$ and halides other than the fluorides.

The semiconductor constituting the electron transporting layer includes one kind alone of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a crystallite or amorphous insulating thin film. If the electron transporting layer is constituted from the above insulating thin film, the more homogeneous thin film is formed, and therefore picture element defects such as dark spots can be reduced. The above inorganic compound includes the alkali metal chalcogenides, the alkaline earth metal chalcogenides, the halides of alkali metals and the halides of alkaline earth metals each described above.

(7) Cathode

Substances using metals, alloys, electroconductive compounds and mixtures thereof each having a small work function (4 eV or less) for the electrode material are used as the cathode in order to inject electrons into the electron injecting and transporting layer or the light emitting layer. The specific examples of the above electrode material include sodium, sodium.cndot.potassium alloys, magnesium, lithium, magnesium.cndot.silver alloys, aluminum/aluminum oxide, aluminum.cndot.lithium alloys, indium and rare earth metals.

The above cathode can be prepared by forming a thin film from the above electrode materials by a method such as vapor deposition, sputtering and the like.

In this respect, when light emitted from the light emitting layer is taken out from the cathode, a light transmittance of the cathode based on light emitted is preferably larger than 10%.

A sheet resistance of the cathode is preferably several hundred $\Omega/\square$ or less, and a film thickness thereof is usually 10 nm to 1 μm, preferably 50 to 200 nm.

(8) Insulating Layer

The organic EL device is liable to cause picture element defects by leak and short circuit. In order to prevent this, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used.

(9) Production Process for Organic EL Device

According to the materials and the forming methods which have been shown above as the examples, the anode, the light emitting layer, if necessary, the hole injecting and transporting layer and, if necessary, the electro injecting and transporting layer are formed, and further the cathode is formed, whereby the organic EL device can be prepared. Also, the organic EL device can be prepared as well from the cathode to the anode in an order which is reverse to what was described above.

A preparation example of an organic EL device having a structure in which an anode/a hole injecting layer/a light emitting layer/an electron injecting layer/a cathode are provided in order on a light transmitting substrate shall be described below.

First, a thin film comprising an anode material is formed on a suitable light transmitting substrate by a method such as deposition, sputtering and the like so that a film thickness falling in a range of 1 μm or less, preferably 10 to 200 nm is obtained, whereby an anode is prepared. Next, a hole injecting layer is provided on this anode. The hole injecting layer can be formed, as described above, by a method such as a vacuum vapor deposition method, a spin coating method, a casting method, an LB method and the like, and it is formed preferably by the vacuum vapor deposition method from the viewpoints that the homogeneous film is liable to be obtained and that pinholes are less liable to be produced. When forming the hole injecting layer by the vacuum vapor deposition method, the depositing conditions thereof are varied according to the compounds used (materials for the hole injecting layer), the crystal structure of the targeted hole injecting layer and the recombination structure, and in general, they are suitably selected preferably in the ranges of a depositing source temperature of 50 to 450° C., a vacuum degree of $10^{-7}$ to $10^{-3}$ Torr, a depositing speed of 0.01 to 50 nm/second, a substrate temperature of −50 to 300° C. and a film thickness of 5 nm to 5 μm.

Next, a light emitting layer can be formed on the hole injecting layer by making a thin film from the desired organic luminescent material by a method such as a vacuum vapor deposition method, sputtering, a spin coating method, a casting method and the like, and it is formed preferably by the vacuum vapor deposition method from the viewpoints that the homogeneous film is liable to be obtained and that pinholes are less liable to be produced. When forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It is formed preferably by the vacuum vapor deposition method as is the case with the hole injecting layer and the light emitting layer since the homogeneous film has to be obtained. The depositing conditions thereof can be selected from the same condition ranges as in the hole injecting layer and the light emitting layer.

The aromatic amine compound of the present invention can be codeposited together with the other materials, though varied depending on that it is added to any layer in the light emitting zone and the hole transporting zone, when using the vacuum vapor deposition method. When using the spin coating method, it can be added by mixing with the other materials.

Lastly, a cathode is laminated, whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The above organic EL device is preferably prepared serially from the anode up to the cathode after being evacuated once.

The forming methods of the respective layers in the organic EL device of the present invention shall not specifically be restricted, and the forming methods carried out by the vacuum vapor deposition method and the spin coating method which have so far publicly been known can be used. The organic thin film layer containing the compound represented by Formula (1) described above which is used for the organic EL device of the present invention can be formed by a publicly known method carried out by a coating method such as a vacuum vapor deposition method, a molecular beam epitaxy method (MBE method) or, using a solution prepared by dissolving the compounds into a solvent, in accordance with a known coating process such as the dipping process, the spin coating process, the casting process, the bar coating process, or the roll coating process.

The film thicknesses of the respective organic layers in the organic EL device of the present invention shall not specifically be restricted, and in general, if the film thicknesses are too small, defects such as pinholes are liable to be caused. On the other hand, if they are too large, high voltage has to be applied, and the efficiency is deteriorated, so that they fall preferably in a range of several nm to 1 µm.

When applying a direct voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only when the anode has a plus polarity and the cathode has a minus polarity. The waveform of an alternating current applied may be optional.

EXAMPLES

The present invention shall be explained in further details below with reference to synthetic examples and examples. Intermediates synthesized in Synthetic Examples 1 to 14 have the following structures:

Intermediate 1

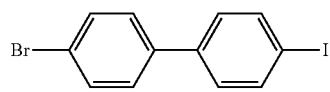

Intermediate 2

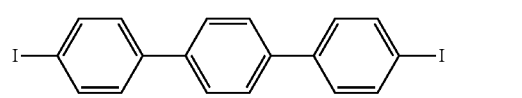

Intermediate 3

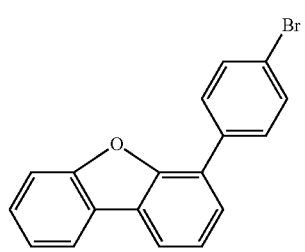

-continued

Intermediate 4

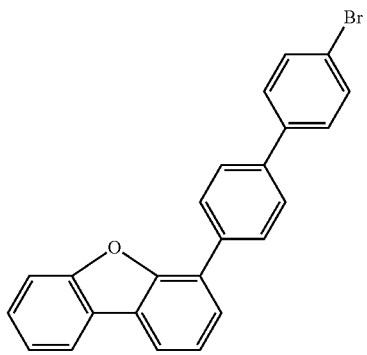

Intermediate 5

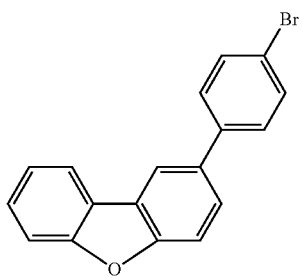

Intermediate 6

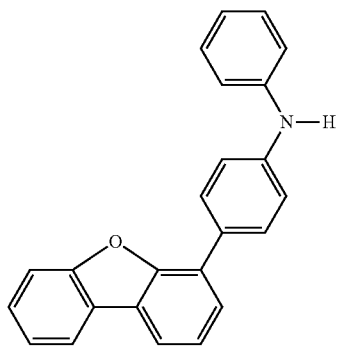

Intermediate 7

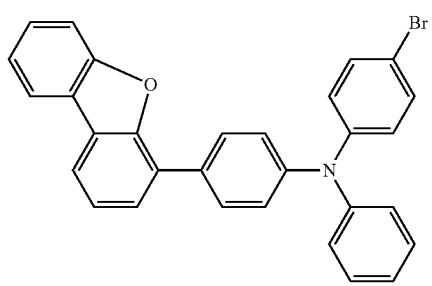

Intermediate 8

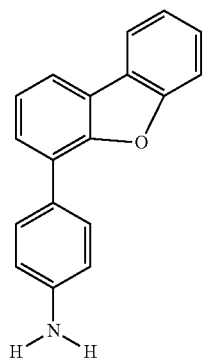

Intermediate 9

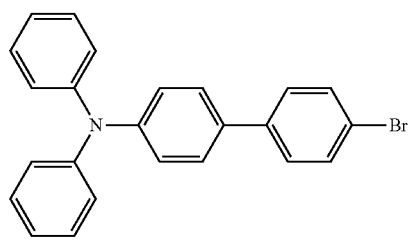

Intermediate 10

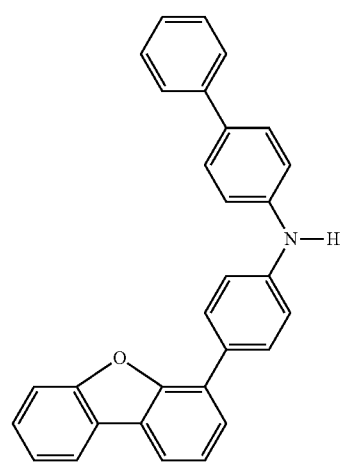

Intermediate 11

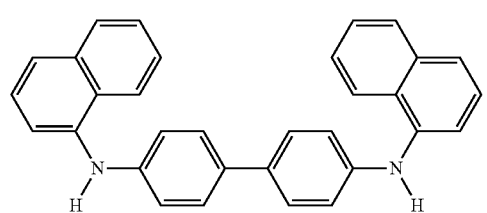

Intermediate 12

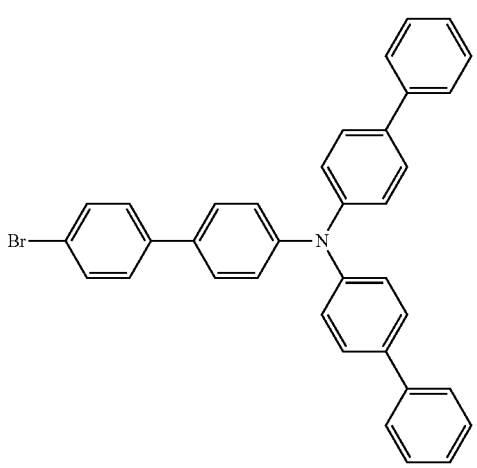

Intermediate 13

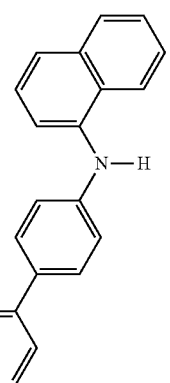

Intermediate 14

Synthetic Example 1

Synthesis of Intermediate 1

A three neck flask of 1000 ml was charged with 47 g of 4-bromobiphenyl, 23 g of iodine, 9.4 g of periodic acid dihydrate, 42 ml of water, 360 mL of acetic acid and 11 mL of sulfuric acid under argon flow, and the mixture was stirred at 65° C. for 30 minutes and then reacted at 90° C. for 6 hours. The reaction product was poured into ice and water and filtered. The filtered matter was washed with water and then with methanol, whereby 67 g of a white powder was obtained. The principal peak of m/z=358 and 360 versus $C_{12}H_{15}BrI=359$ was obtained by analysis of FD-MS, and therefore it was identified as the intermediate 1.

Synthetic Example 2

Synthesis of Intermediate 2

A three neck flask of 300 ml was charged with 10 g of p-terphenyl, 12 g of iodine, 4.9 g of periodic acid dihydrate, 20 mL of water, 170 mL of acetic acid and 22 mL of sulfuric acid under argon flow, and the mixture was stirred at 65° C. for 30 minutes and then reacted at 90° C. for 6 hours. The reaction product was poured into ice and water and filtered. The filtered matter was washed with water and then with methanol, whereby 18 g of a white powder was obtained. The principal peak of m/z=482 versus $C_{18}H_{12}I_2=482$ was obtained by analysis of FD-MS, and therefore it was identified as the intermediate 2.

Synthetic Example 3

Synthesis of Intermediate 3

A three neck flask of 1000 ml was charged with 42.4 g of 4-dibenzofuranboronic acid, 56.0 g of 4-iodobromobenzene, 6.9 g of tetrakis-(triphenylphosphine)palladium ($Pd(PPh_3)_4$), 320 mL of a sodium carbonate ($Na_2CO_3$) solution of 2M and 320 mL of toluene under argon flow, and then they were reacted at 80° C. for 8 hours. The reaction solution was extracted with toluene/water, and the extract was dried on anhydrous sodium sulfate. This was concentrated under reduced pressure, and a crude product obtained was refined through a column, whereby 28.5 g of a white powder was obtained. It was identified as the intermediate 3 by analysis of FD-MS.

Synthetic Example 4

Synthesis of Intermediate 4

Reaction was carried out in the same manner, except that in Synthetic Example 3, 71 g of the intermediate 1 was used in place of 4-iodobromobenzene, whereby 42.4 g of a white powder was obtained. It was identified as the intermediate 4 by analysis of FD-MS.

Synthetic Example 5

Synthesis of Intermediate 5

A three neck flask of 500 ml was charged with 24.9 g of 2-bromodibenzofuran obtained by a synthetic method described in a document (J. Org. Chem., 62, 5, 1997, 1348 to 1355), 80 mL of dehydrated ether and 80 mL of dehydrated toluene under argon flow. 120 mmol of a n-butyllithium/hexane solution was poured thereinto at −30° C. to carry out reaction at 0° C. for one hour. The reaction solution was cooled down to −70° C., and 70 mL of triisopropyl borate ($B(OiPr)_3$) was poured thereinto. The solution was heated slowly up to room temperature and stirred for one hour. The solution to which 80 mL of 10% hydrochloric acid was added was extracted with ethyl acetate/water, and then the extract was dried on anhydrous sodium sulfate. The solution was concentrated and washed with hexane to thereby obtain 10.4 g of a boronic acid compound.

Reaction was carried out in the same manner, except that in Synthetic Example 3, 42.4 g of 2-dibenzofuranboronic acid obtained above was used in place of 4-dibenzofuranboronic acid, whereby 24.6 g of a white powder was obtained. It was identified as the intermediate 5 by analysis of FD-MS.

Synthetic Example 6

Synthesis of Intermediate 6

A flask was charged with 5.5 g of aniline, 16.2 g of the intermediate 3, 6.8 g of sodium t-butoxide (manufactured by Hiroshima Wako Co., Ltd.), 0.46 g of tris(dibenzylideneacetone)dipalladium (0) (manufactured by Aldrich Co., Ltd.) and 300 mL of dehydrated toluene under argon flow to carry out reaction at 80° C. for 8 hours.

After cooling down, 500 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 10.1 g of a pale yellow powder was obtained. It was identified as the intermediate 6 by analysis of FD-MS.

Synthetic Example 7

Synthesis of Intermediate 7

A flask was charged with 10 g of the intermediate 6, 8.8 g of 1-bromo-4-iodobenzene (manufactured by Aldrich Co., Ltd.), 3 g of sodium t-butoxide (manufactured by Hiroshima Wako Co., Ltd.), 0.5 g of bis(triphenylphosphine)palladium chloride (II) (manufactured by Tokyo Kasei Kogyo Co., Ltd.) and 500 ml of xylene under argon flow to carry out reaction at 130° C. for 24 hours.

After cooling down, 1000 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 3.2 g of a pale yellow powder was obtained. It was identified as the intermediate 7 by analysis of FD-MS.

Synthetic Example 8

Synthesis of Intermediate 8

Reaction was carried out in the same manner, except that in Synthetic Example 3, 71 g of 4-bromoaniline was used in place of 4-iodobromobenzene, whereby 26.4 g of a white powder was obtained. It was identified as the intermediate 8 by analysis of FD-MS.

Synthetic Example 9

Synthesis of Intermediate 9

Reaction was carried out in the same manner, except that in Synthetic Example 7, 5.2 g of diphenylamine was used in place of the intermediate 3 and that 11.0 g of the intermediate 1 was used in place of 1-bromo-4-iodobenzene, whereby 2.6 g of a white powder was obtained. It was identified as the intermediate 9 by analysis of FD-MS.

Synthetic Example 10

Synthesis of Intermediate 10

Reaction was carried out in the same manner, except that in Synthetic Example 6, 13.0 g of the intermediate 8 was used in place of aniline and that 11.6 g of 4-bromobiphenyl was used in place of the intermediate 4, whereby 13.1 g of a white powder was obtained. It was identified as the intermediate 10 by analysis of FD-MS.

Synthetic Example 11

Synthesis of Intermediate 11

A flask was charged with 547 g of 1-acetamidenaphthalene (manufactured by Tokyo Kasei Kogyo Co., Ltd.), 400 g of 4,4'-diiodobiphenyl (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.) and 2 L of decalin under argon flow to carry out reaction at 190° C. for 4 days.

The reaction solution was cooled down after reaction, and insoluble matters were obtained by filtration. The filtered matter was dissolved in 4.5 L of toluene to remove insoluble matters, and then it was subjected to activated carbon treatment and concentrated. Acetone 3 L was added thereto to obtain 382 g of deposited crystal by filtration.

This was suspended in 5 L of ethylene glycol (manufactured by Wako Pure Chemical Industries, Ltd.) and 50 mL of water, and 145 g of a 85% potassium hydroxide aqueous solution was added thereto, followed by carrying out reaction at 120° C. for 2 hours.

After finishing the reaction, the reaction liquid was poured into 10 L of water, and deposited crystal was obtained by filtration and washed with water and methanol.

The crystal thus obtained was dissolved in 3 L of tetrahydrofuran by heating. The solution was treated with activated carbon black and then concentrated, and acetone was added thereto to deposit crystal. This was separated by filtration to obtain 264 g of a white powder. It was identified as the intermediate 11 by analysis of FD-MS.

Synthetic Example 12

Synthesis of Intermediate 12

A three neck flask of 200 ml was charged with 20.0 g of 4-bromobiphenyl (manufactured by Tokyo Kasei Kogyo Co., Ltd.), 8.64 g of sodium t-butoxide (manufactured by Wako Pure Chemical Industries, Ltd.) and 84 mg of palladium acetate (manufactured by Wako Pure Chemical Industries, Ltd.). Further, a stirring rod was put therein, and rubber caps were set at both sided of the flask. A Gimroth condenser for refluxing was set in the neck of the center, and a three-way cock and a balloon charged with argon gas were set thereon to substitute the inside of the system three times with the argon gas in the balloon by means of a vacuum pump.

Next, 120 mL of dehydrated toluene (manufactured by Hiroshima Wako Co., Ltd.), 4.08 mL of benzylamine (manufactured by Tokyo Kasei Kogyo Co., Ltd.) and 338 µL of tris-t-butylphsosphine (a 2.22 mol/L toluene solution, manufactured by Aldrich Co., Ltd.) were added thereto through a rubber septum by means of a syringe and stirred at room temperature for 5 minutes. Next, the flask was set on an oil bath and gradually heated up to 120° C. while stirring the solution. After 7 hours passed, the flask was taken off from the oil bath to terminate the reaction, and it was left standing for 12 hours under argon atmosphere. The reaction solution was transferred into a separating funnel, and 600 mL of dichloromethane was added thereto to dissolve the precipitate. The organic layer was washed with 120 mL of a saturated brine and then dried on anhydrous potassium carbonate. The solvent of the organic layer obtained by filtering off potassium carbonate was distilled off, and 400 mL of toluene and 80 mL of ethanol were added to the resulting residue. The flask to which a drying tube was mounted was heated to 80° C. to completely dissolve the residue. Then, the flask was left standing for 12 hours and slowly cooled down to room temperature to thereby expedite recrystallization. Deposited crystal was separated by filtration and dried under vacuum at 60° C., whereby 13.5 g of N,N-di-(4-biphenylyl)-benzylamine was obtained. A single neck flask of 300 mL was charged with 1.35 g of N,N-di-(4-biphenylyl)-benzylamine and 135 mg of palladium-activated carbon black (palladium content: 10% by weight, manufactured by Hiroshima Wako Co., Ltd.), and 100 mL of chloroform and 20 mL of ethanol were added to dissolve it. Next, a stirring rod was put in the flask, and then a three-way cock which was equipped a balloon charged with 2 L of hydrogen gas was mounted to the flask. The inside of the flask was substituted 10 times with hydrogen gas by means of a vacuum pump. Lost hydrogen gas was newly charged to set again a volume of hydrogen gas to 2 L, and then the solution was vigorously stirred at room temperature. After stirring for 30 hours, 100 mL of dichloromethane was added thereto to separate the catalyst by filtration. Next, the solution obtained was transferred into a separating funnel and washed with 50 mL of a sodium hydrogencarbonate saturated aqueous solution, and then the organic layer was separated and dried on anhydrous potassium carbonate. After filtered, the solvent was distilled off, and 50 mL of toluene was added to the resulting residue to carry out recrystallization. Deposited crystal was separated by filtration and dried under vacuum at 50° C., whereby 0.99 g of di-4-biphenylylamine was obtained.

A flask was charged with 10 g of di-4-biphenylylamine, 9.7 g of 4,4'-dibromobiphenyl (manufactured by Tokyo Kasei Kogyo Co., Ltd.), 3 g of sodium t-butoxide (manufactured by Hiroshima Wako Co., Ltd.), 0.5 g of bis(triphenylphosphine) palladium chloride (II) (manufactured by Tokyo Kasei Kogyo Co., Ltd.) and 500 ml of xylene under argon flow to carry out reaction at 130° C. for 24 hours. After cooling down, 1000 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 9.1 g of 4'-bromo-N,N-dibiphenylyl-4-amino-1,1'-biphenyl (intermediate 12).

Synthetic Example 13

Synthesis of Intermediate 13

Reaction was carried out in the same manner, except that in Synthetic Example 10, 8.0 g of 1-bromonaphthalene was used in place of 4-bromobiphenyl, whereby 9.6 g of a white powder was obtained. It was identified as the intermediate 13 by analysis of FD-MS.

Synthetic Example 14

Synthesis of Intermediate 14

Reaction was carried out in the same manner, except that in Synthetic Example 10, 16.1 g of the intermediate 3 was used in place of 4-bromobiphenyl, whereby 10.5 g of a white powder was obtained. It was identified as the intermediate 14 by analysis of FD-MS.

Compounds H1 to 15 which are the aromatic amine derivatives of the present invention synthesized in the following Synthetic Practical Examples 1 to 15 and a comparative compound 1 used in Comparative Example 1 have the following structures:

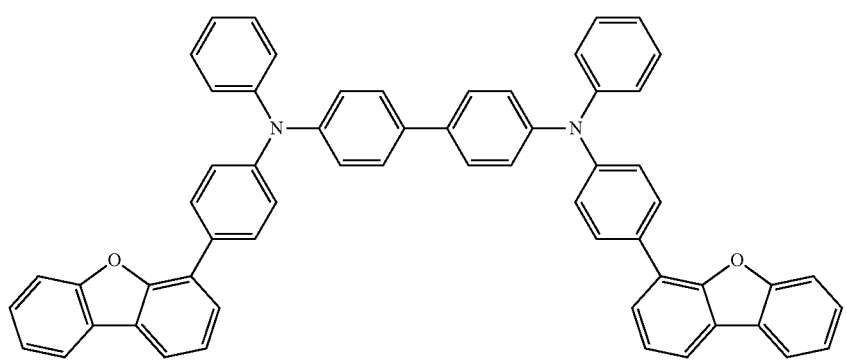

H1

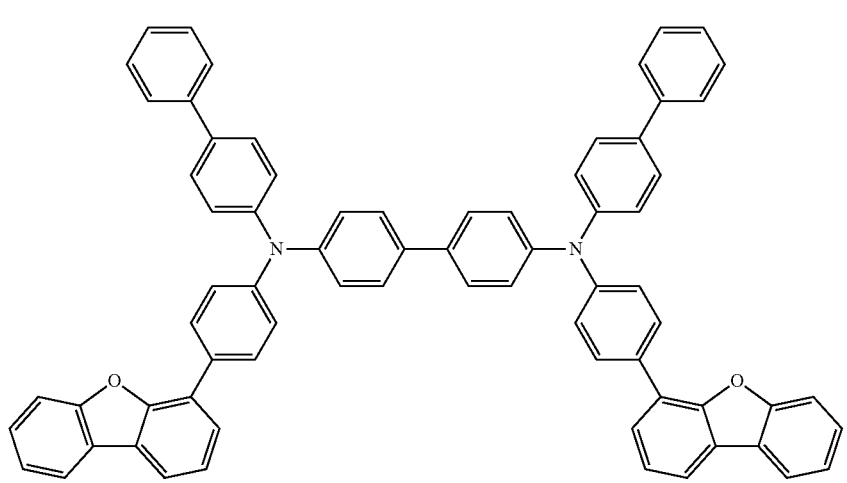

H2

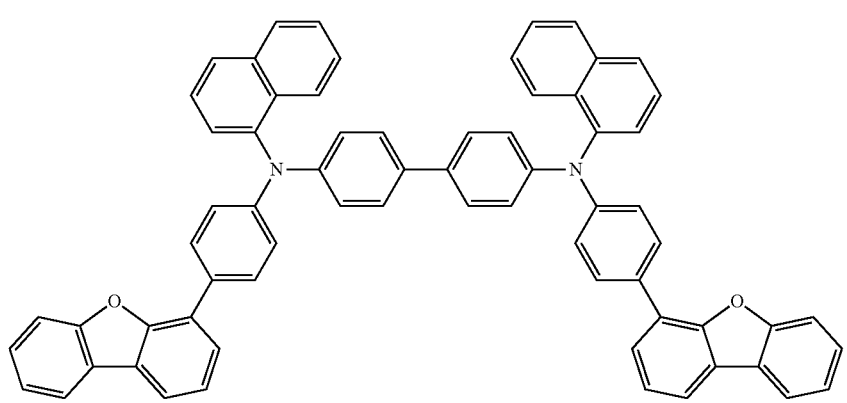

H3

-continued
H4
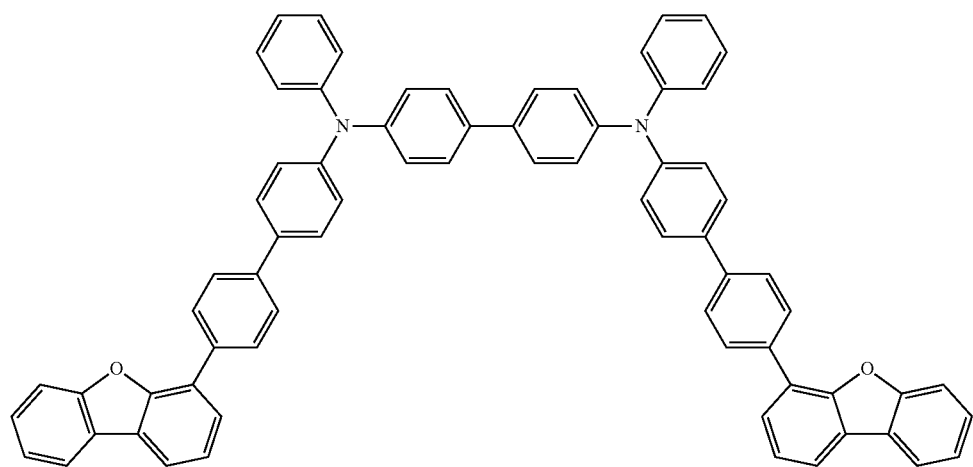
H5
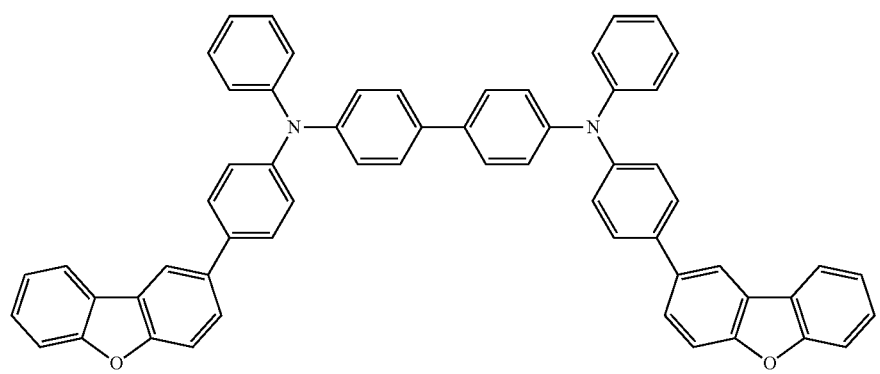
H6
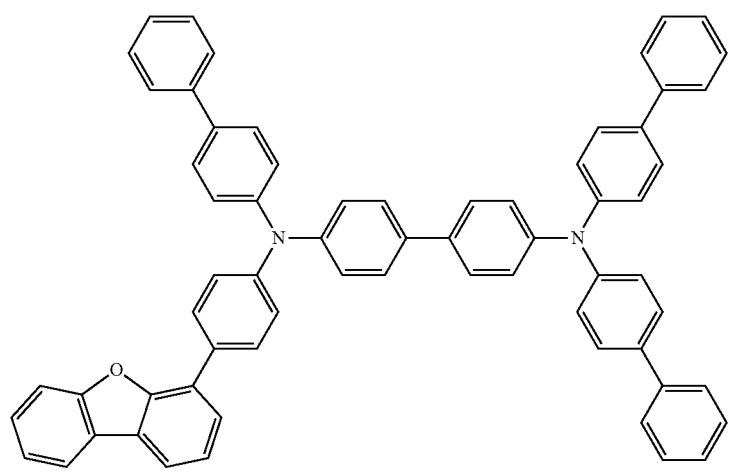

-continued
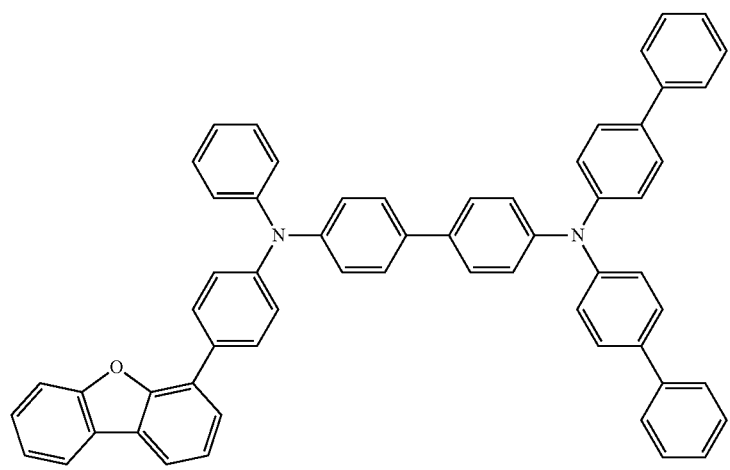
H7
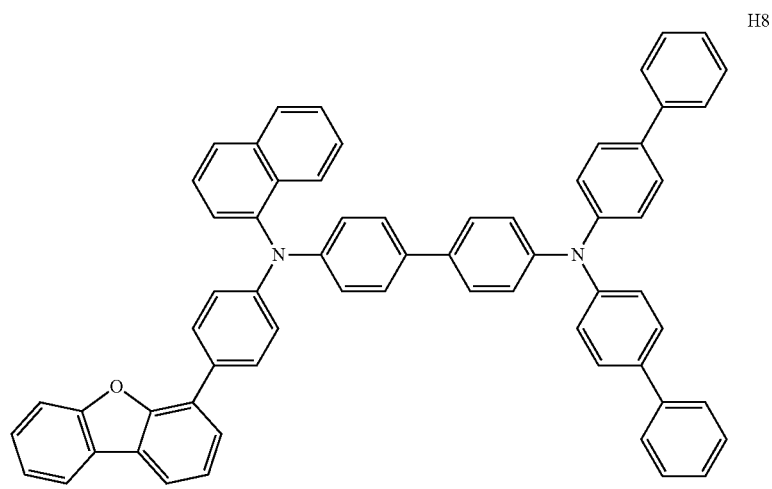
H8
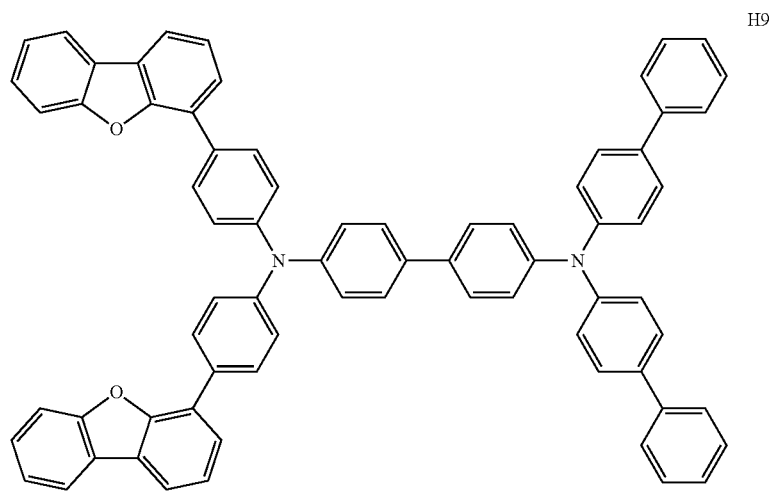
H9

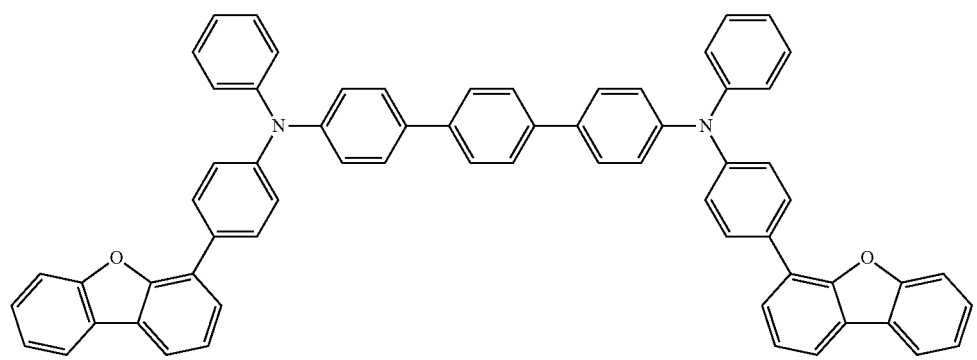
H10
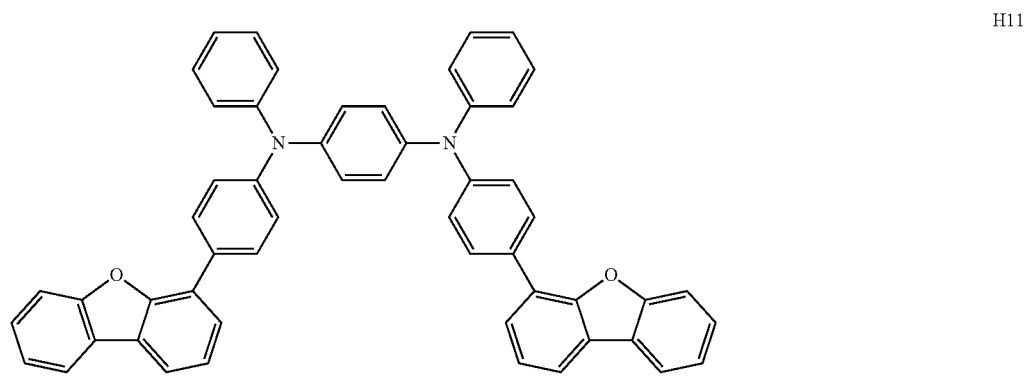
H11
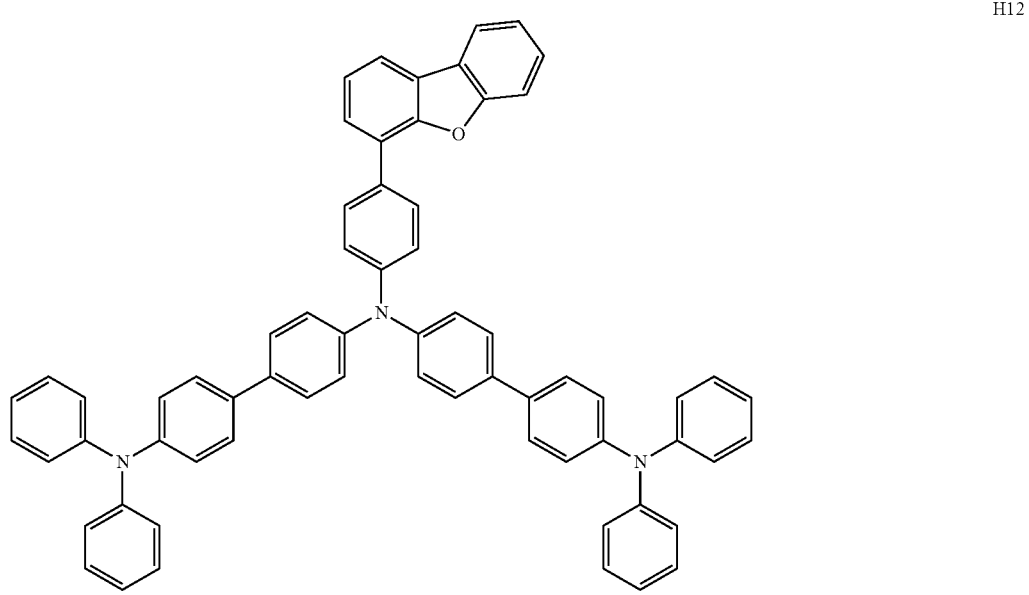
H12

H13
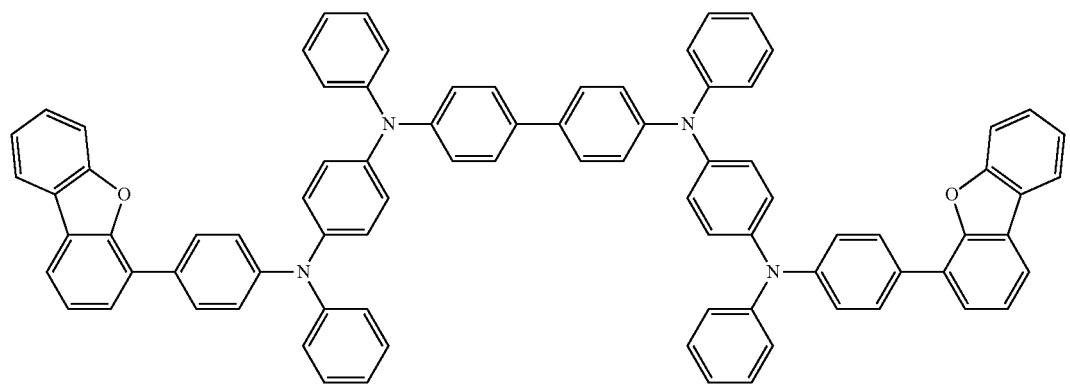
H14
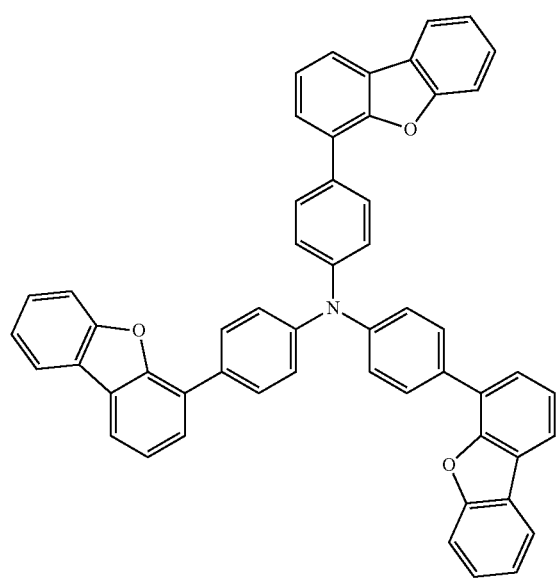
H15
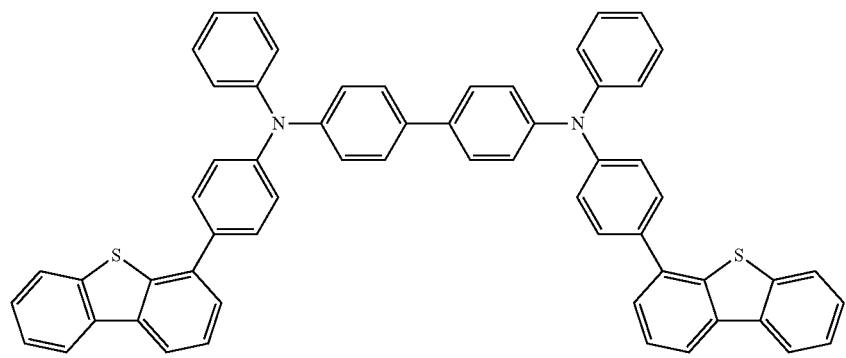

Comparative Compound 1

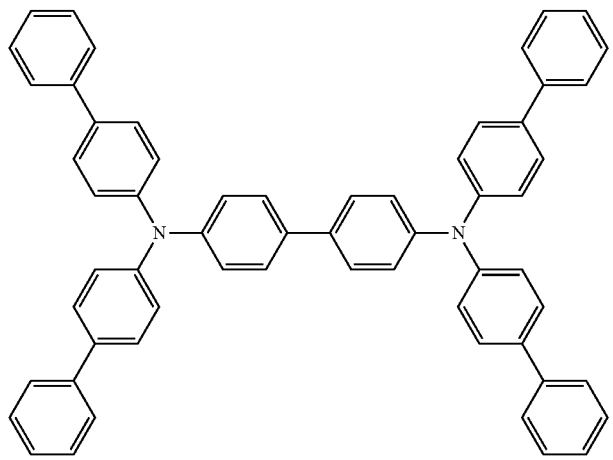

Synthetic Practical Example 1

Synthesis of Compound H1

A flask was charged with 3.4 g of N,N'-diphenylbenzidine, 6.8 g of the intermediate 3, 2.6 g of sodium t-butoxide (manufactured by Hiroshima Wako Co., Ltd.), 92 mg of tris(dibenzylideneacetone)-dipalladium (0) (manufactured by Aldrich Co., Ltd.), 42 mg of tri-t-butylphosphine and 100 mL of dehydrated toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 4.1 g of a pale yellow powder was obtained. It was identified as the compound H1 by analysis of FD-MS (field desorption mass spectrum).

Synthetic Practical Example 2

Synthesis of Compound H2

A flask was charged with 4.1 g of 4,4'-diiodobiphenyl, 7.0 g of the intermediate 8, 2.6 g of sodium t-butoxide (manufactured by Hiroshima Wako Co., Ltd.), 92 mg of tris(dibenzylideneacetone)-dipalladium (0) (manufactured by Aldrich Co., Ltd.), 42 mg of tri-t-butylphosphine and 100 mL of dehydrated toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 4.9 g of a pale yellow powder was obtained. It was identified as the compound H2 by analysis of FD-MS (field desorption mass spectrum).

Synthetic Practical Example 3

Synthesis of Compound H3

Reaction was carried out in the same manner, except that in Synthetic Practical Example 1, 4.4 g of the intermediate 11 was used in place of N,N-diphenylbenzidine, whereby 5.2 g of a pale yellow powder was obtained. It was identified as the compound H3 by analysis of FD-MS.

Synthetic Practical Example 4

Synthesis of Compound H4

Reaction was carried out in the same manner, except that in Synthetic Practical Example 1, 8.4 g of the intermediate 4 was used in place of the intermediate 3, whereby 4.6 g of a pale yellow powder was obtained. It was identified as the compound H4 by analysis of FD-MS.

Synthetic Practical Example 5

Synthesis of Compound H5

Reaction was carried out in the same manner, except that in Synthetic Practical Example 1, 6.8 g of the intermediate 5 was used in place of the intermediate 3, whereby 3.9 g of a pale yellow powder was obtained. It was identified as the compound H5 by analysis of FD-MS.

Synthetic Practical Example 6

Synthesis of Compound H6

A flask was charged with 8.2 g of the intermediate 10, 11.0 g of the intermediate 12, 2.6 g of sodium t-butoxide (manufactured by Hiroshima Wako Co., Ltd.), 92 mg of tris(dibenzylideneacetone)-dipalladium (0) (manufactured by Aldrich Co., Ltd.), 42 mg of tri-t-butylphosphine and 100 mL of dehydrated toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 13.1 g of a pale yellow powder was obtained. It was identified as the compound H6 by analysis of FD-MS (field desorption mass spectrum).

Synthetic Practical Example 7

Synthesis of Compound H7

Reaction was carried out in the same manner, except that in Synthetic Practical Example 6, 6.5 g of the intermediate 6 was used in place of the intermediate 10, whereby 8.2 g of a pale yellow powder was obtained. It was identified as the compound H7 by analysis of FD-MS.

Synthetic Practical Example 8

Synthesis of Compound H8

Reaction was carried out in the same manner, except that in Synthetic Practical Example 6, 7.7 g of the intermediate 13 was used in place of the intermediate 10, whereby 10.2 g of a pale yellow powder was obtained. It was identified as the compound H8 by analysis of FD-MS.

Synthetic Practical Example 9

Synthesis of Compound H9

Reaction was carried out in the same manner, except that in Synthetic Practical Example 6, 10.3 g of the intermediate 14 was used in place of the intermediate 10, whereby 15.1 g of a pale yellow powder was obtained. It was identified as the compound H9 by analysis of FD-MS.

Synthetic Practical Example 10

Synthesis of Compound H10

Reaction was carried out in the same manner, except that in Synthetic Practical Example 2, 4.8 g of dibromoterphenyl was used in place of 4,4'-diiodobiphenyl and that 7.0 g of the intermediate 6 was used in place of the intermediate 10, whereby 4.8 g of a pale yellow powder was obtained. It was identified as the compound H10 by analysis of FD-MS.

Synthetic Practical Example 11

Synthesis of Compound H11

Reaction was carried out in the same manner, except that in Synthetic Practical Example 2, 3.3 g of 1,4-diiodobenzene was used in place of 4,4'-diiodobiphenyl, whereby 4.1 g of a pale yellow powder was obtained. It was identified as the compound H11 by analysis of FD-MS.

Synthetic Practical Example 12

Synthesis of Compound H12

Reaction was carried out in the same manner, except that in Synthetic Practical Example 1, 2.6 g of the intermediate 10 was used in place of N,N'-diphenylbenzidine and that 8.4 g of the intermediate 9 was used in place of the intermediate 3, whereby 5.9 g of a pale yellow powder was obtained. It was identified as the compound H12 by analysis of FD-MS.

Synthetic Practical Example 13

Synthesis of Compound H13

Reaction was carried out in the same manner, except that in Synthetic Practical Example 1, 10.3 g of the intermediate 7 was used in place of the intermediate 3, whereby 6.5 g of a pale yellow powder was obtained. It was identified as the compound H13 by analysis of FD-MS.

Synthetic Practical Example 14

Synthesis of Compound H14

A three neck flask of 300 ml was charged with 6.3 g of 4-dibenzofuranboronic acid, 4.8 g of 4,4',4''-tribromotriphenylamine, 104 mg of tetrakis-(triphenylphosphine)palladium ($Pd(PPh_3)_4$), 48 mL of a sodium carbonate ($Na_2CO_3$) solution of 2M and 48 mL of toluene under argon flow, and then they were reacted at 80° C. for 8 hours. The reaction liquid was extracted with toluene/water, and the extract was dried on anhydrous sodium sulfate. This was concentrated under reduced pressure, and a crude product obtained was refined through a column, whereby 3.9 g of a whitish yellow powder was obtained. It was identified as the compound H14 by analysis of FD-MS.

Synthetic Practical Example 15

Synthesis of Compound H15

Reaction was carried out in the same manner, except that in Synthetic Practical Example 10, 6.8 g of 4-dibenzothiopheneboronic acid was used in place of 4-dibenzofuranboronic acid and that 5.1 g of N,N'-diphenylbenzidine was used in place of 4,4',4''-tribromotriphenylamine, whereby 7.2 g of a pale yellow powder was obtained. It was identified as the compound H15 by analysis of FD-MS.

Example 1

Production of Organic EL Device

A glass substrate (manufactured by Geomatech Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes.

After washed, the glass substrate equipped with an ITO transparent electrode line was loaded in a substrate holder of a vacuum vapor deposition apparatus, and a film of a compound H232 shown below having a film thickness of 60 nm was formed on a face of a side at which the transparent electrode line was formed so that it covered the transparent electrode described above. This H232 film functions as a hole injecting layer. A film of the compound H1 described above having a film thickness of 20 nm was formed as a hole transporting material on the above H232 film. This film functions as a hole transporting layer. Further, a compound EM1 shown below was deposited thereon to form a film having a film thickness of 40 nm. At the same time, the following amine compound D1 having a styryl group was deposited as a light emitting molecule so that a weight ratio of EM1 to D1 was 40:2. This film functions as a light emitting layer.

A film of Alq shown below having a film thickness of 10 nm was formed on the above film. This film functions as an electron injecting layer. Then, Li (Li source: manufactured by Saesgetter Co., Ltd.) which was a reducing dopant and Alq shown below were subjected to binary vapor deposition to form an Alq:Li film (film thickness: 10 nm) as an electron injecting layer (cathode). Metal Al was deposited on the above Alq:Li film to form a metal cathode, whereby an organic EL device was formed.

Further, the organic EL device thus obtained was measured for a current efficiency and observed for a luminescent color. The luminance was measured by means of CS1000 manufactured by Konica Minolta Co., Ltd. to calculate the current efficiency at 10 mA/cm$^2$. Further, the half lifetime thereof in light emission was measured at an initial luminance of 5000 cd/m$^2$ and room temperature in operating at a DC constant electric current, and the results thereof are shown in Table 1.

Examples 2 to 9

Production of Organic EL Devices

Organic EL devices were prepared in the same manner, except that in Example 1, compounds described in Table 1 were used as hole transporting materials in place of the compound H1.

The organic EL devices thus obtained were measured for a current efficiency and observed for a luminescent color. Further, the half lifetimes thereof in light emission were measured at an initial luminance of 5000 cd/m$^2$ and room temperature in operating at a DC constant electric current, and the results thereof are shown in Table 1.

Comparative Example 1

An organic EL device was prepared in the same manner, except that in Example 1, a comparative compound 1 (Com-

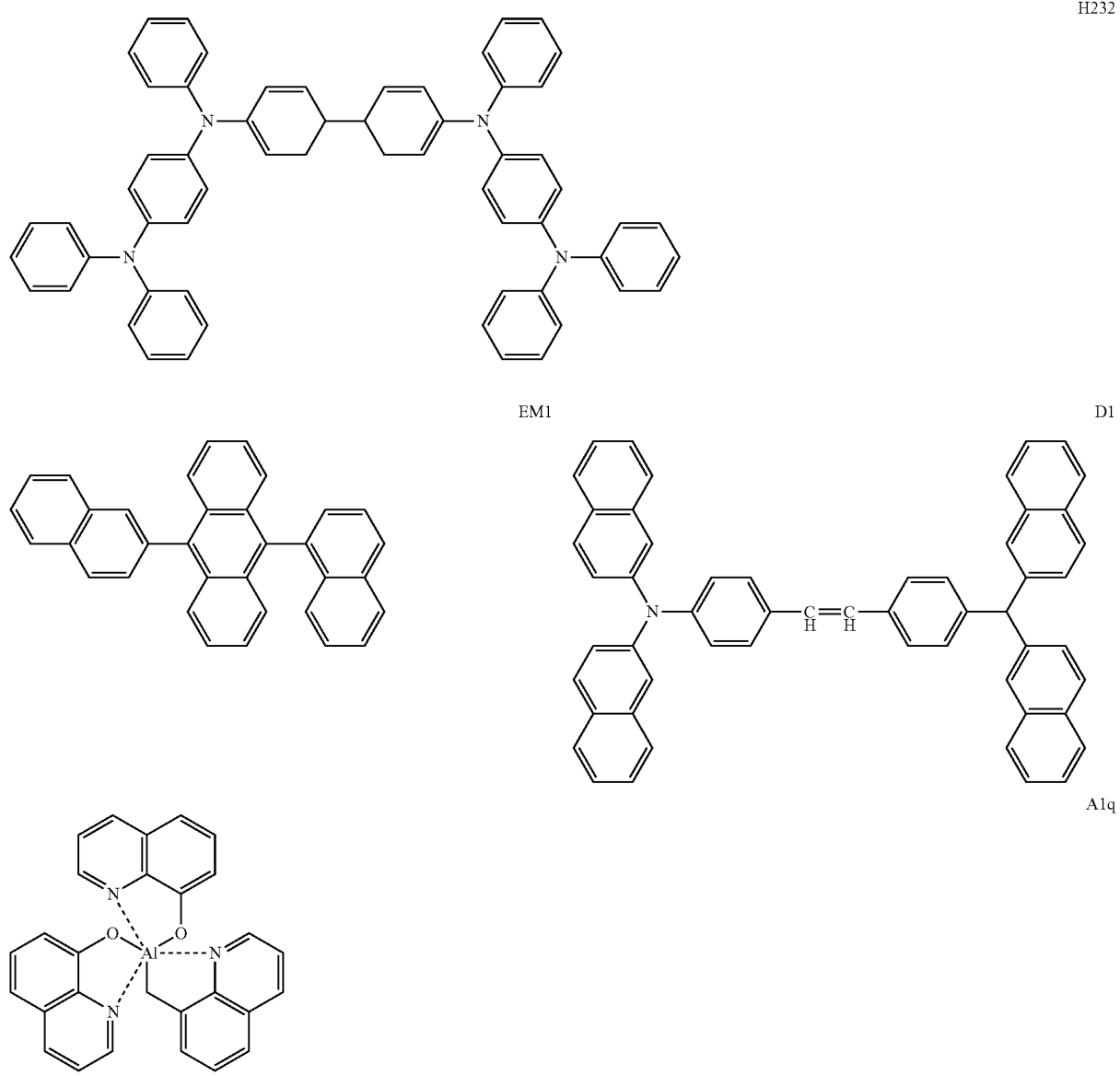

parative Example 1) was used as a hole transporting material in place of the compound H1. The comparative compound 1 was crystallized in vapor deposition, and a normal device could not be prepared.

The organic EL device obtained was measured for a current efficiency and observed for a luminescent color, and the half lifetime thereof in light emission was measured at an initial luminance of 5000 cd/m² and room temperature in operating at a DC constant electric current, and the results thereof are shown in Table 1.

TABLE 1

|  | Hole transporting material | Current efficiency (cd/A) | Luminescent color | Half lifetime (hour) |
|---|---|---|---|---|
| Example 1 | H1 | 5.1 | blue | 440 |
| Example 2 | H2 | 5.1 | blue | 420 |
| Example 3 | H3 | 4.9 | blue | 370 |
| Example 4 | H4 | 5.0 | blue | 410 |
| Example 5 | H5 | 4.8 | blue | 400 |
| Example 6 | H6 | 5.0 | blue | 420 |
| Example 7 | H7 | 5.1 | blue | 440 |
| Example 8 | H8 | 4.8 | blue | 380 |
| Example 9 | H9 | 5.1 | blue | 410 |
| Comparative Example 1 | Comparative compound 1 | 5.1 | blue | 280 |

Example 10

Production of Organic EL Device

An organic EL device was prepared in the same manner, except that in Example 1, the following compound D2 having a styryl group was used in place of the amine compound D1. Me represents methyl.

The organic EL device thus obtained was measured for a current efficiency to find that it was 4.9 cd/A and that a luminescent color was blue. Further, the half lifetime thereof in light emission was measured at an initial luminance of 5000 cd/m² and room temperature in operating at a DC constant electric current to find that it was 430 hours.

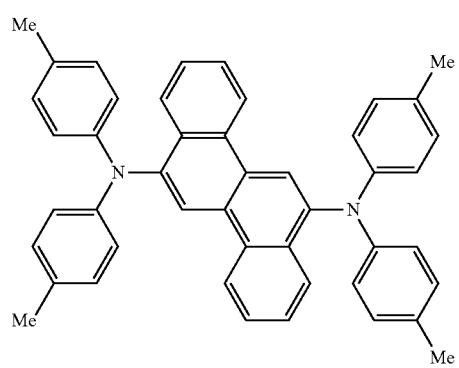

D2

Comparative Example 2

An organic EL device was prepared in the same manner, except that in Example 10, the comparative compound 1 described above was used as a hole transporting material in place of the compound H1.

The organic EL device thus obtained was measured for a current efficiency to find that it was 4.9 cd/A and that a luminescent color was blue. Further, the half lifetime thereof in light emission was measured at an initial luminance of 5000 cd/m² and room temperature in operating at a DC constant electric current to find that it was 260 hours.

Example 11

Production of Organic EL Element

An organic EL device was prepared in the same manner, except that in Example 1, H1 was used in place of H232 and that the comparative compound 1 described above was used in place of H1.

The organic EL device thus obtained was measured for a current efficiency to find that it was 5.1 cd/A and that a luminescent color was blue. Further, the half lifetime thereof in light emission was measured at an initial luminance of 5000 cd/m² and room temperature in operating at a DC constant electric current to find that it was 360 hours.

INDUSTRIAL APPLICABILITY

As explained above in details, the aromatic amine derivative of the present invention is less liable to be crystallized in molecules, and addition thereof to the organic thin film layer enhances a yield in producing the organic EL device and makes it possible to materialize the organic EL device having a long lifetime.

What is claimed is:

1. An aromatic amine compound represented by Formula (5):

(5)

wherein at least one of Ar₇ to Ar₉ is represented by the following Formula (3):

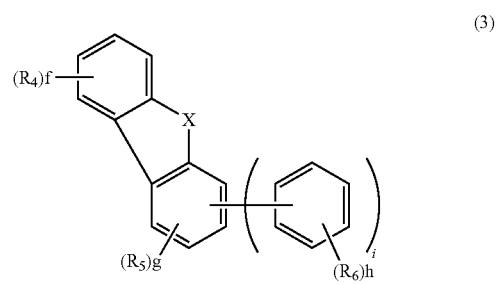

(3)

wherein R₄ is a hydrogen atom, non-substituted aryl group having 5 to 50 ring carbon atoms, a substituted aryl group having 5 to 50 ring carbon atoms which said substituted aryl group is substituted by an alkyl group having 1 to 4 carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 2 to 50 carbon atoms, a halogen atom, a cyano group, a nitro group, a hydroxyl group or a carboxyl group;

$R_5$ and $R_6$ each are independently a hydrogen atom, an unsubstituted aryl group having 5 to 50 ring carbon atoms, an aryl group having 5 to 50 ring carbon atoms that is substituted with an alkyl group having 1 to 4 carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 2 to 50 carbon atoms, an amino group substituted with a substituted or unsubstituted aryl group having 5 to 50 ring carbon atoms, a halogen atom, a cyano group, a nitro group, a hydroxyl group or a carboxyl group;

X is an oxygen atom;

f and h each are an integer of 0 to 4;

g is an integer of 0 to 3; and i is an integer of 1 to 3;

plural $R_4$ or $R_5$ or $R_6$ may be combined with each other to form a cyclic structure of a saturated or unsaturated five-membered ring or six-membered ring which may be substituted;

when i is 2 or more and h is not 0, plural $R_6$ may be combined with each other to form a cyclic structure of a saturated or unsaturated five-membered ring or six-membered ring which may be substituted);

in Formula (5), among $Ar_7$ to $Ar_9$, the groups which are not represented by Formula (3) each are independently a substituted or unsubstituted aryl group having 5 to 50 ring carbon atoms.

2. The aromatic amine compound of claim 1, wherein among $Ar_7$ to $Ar_9$, the groups which are not represented by Formula (3) each are independently an unsubstituted aryl group having 5 to 50 ring carbon atoms.

3. The aromatic amine compound of claim 1, wherein f, g, and h are 0.

4. The aromatic amine compound of claim 1, wherein $R_4$ is a hydrogen atom, an unsubstituted aryl group having 5 to 50 ring carbon atoms, an aryl group having 5 to 50 ring carbon atoms that is substituted by an alkyl group having 1 to 4 carbon atoms, an unsubstituted alkyl group having 1 to 50 carbon atoms, an unsubstituted alkoxy group having 1 to 50 carbon atoms, an unsubstituted aralkyl group having 6 to 50 carbon atoms, an unsubstituted aryloxy group having 5 to 50 ring carbon atoms, an unsubstituted arylthio group having 5 to 50 ring carbon atoms, an unsubstituted alkoxycarbonyl group having 2 to 50 carbon atoms, a halogen atom, a cyano group, a nitro group, a hydroxyl group or a carboxyl group;

$R_5$ and $R_6$ each are independently a hydrogen atom, an unsubstituted aryl group having 5 to 50 ring carbon atoms, an aryl group having 5 to 50 ring carbon atoms that is substituted by an alkyl group having 1 to 4 carbon atoms, an substituted alkyl group having 1 to 50 carbon atoms, an substituted alkoxy group having 1 to 50 carbon atoms, an substituted aralkyl group having 6 to 50 carbon atoms, an substituted aryloxy group having 5 to 50 ring carbon atoms, an substituted arylthio group having 5 to 50 ring carbon atoms, an unsubstituted alkoxycarbonyl group having 2 to 50 carbon atoms, an amino group substituted with an unsubstituted aryl group having 5 to 50 ring carbon atoms, a halogen atom, a cyano group, a nitro group, a hydroxyl group or a carboxyl group;

plural $R_4$ or $R_5$ or $R_6$ may be combined with each other to form a cyclic structure of a saturated or unsaturated five-membered ring or six-membered ring;

when i is 2 or 3 and h is not 0, plural $R_6$ may be combined with each other to form a cyclic structure of a saturated or unsaturated five-membered ring or six-membered ring;

in Formula (5), among $Ar_7$ to $Ar_9$, the groups which are not represented by Formula (3) each are independently an substituted aryl group having 5 to 50 ring carbon atoms.

5. The aromatic amine compound of claim 1, wherein among $Ar_7$ to $Ar_9$, the groups which are not represented by Formula (3) are independently selected from the group consisting of a phenyl group, a naphtyl group, a biphenylyl group, an anthranyl group, a phenanthryl group, a pyrenyl group, a chrysenyl group, a fluoranthenyl group and a fluorenyl group, each being optionally substituted.

6. The aromatic amine compound of claim 1, wherein among $Ar_7$ to $Ar_9$, the groups which are not represented by Formula (3) are independently selected from the group consisting of a phenyl group, a biphenylyl group, a terphenylyl group, and a 9,9-dimethyl fluorenyl group, each being optionally substituted.

7. The aromatic amine compound of claim 1, wherein among $Ar_7$ to $Ar_9$, the groups which are not represented by Formula (3) are independently selected from the group consisting of a phenyl group, a naphtyl group, and a biphenylyl group, each being optionally substituted.

8. The aromatic amine compound of claim 1, wherein among $Ar_7$ to $Ar_9$, the groups which are not represented by Formula (3) are independently selected from the group consisting of an unsubstituted phenyl group, an unsubstituted biphenylyl group, an unsubstituted terphenylyl group, and an unsubstituted 9,9-dimethyl fluorenyl group.

9. The aromatic amine compound of claim 1,
wherein $Ar_7$ is represented by Formula (3),
$Ar_8$ is selected from the group consisting of a phenyl group, a biphenylyl group, a terphenylyl group, and a 9,9-dimethyl fluorenyl group, each being optionally substituted, and
$Ar_9$ is selected from the group consisting of a biphenylyl group, a terphenylyl group, and a 9,9-dimethyl fluorenyl group, each being optionally substituted.

10. The aromatic amine compound of claim 1,
wherein $Ar_7$ is represented by Formula (3),
$Ar_8$ is selected from the group consisting of an unsubstituted phenyl group, an unsubstituted biphenylyl group, an unsubstituted terphenylyl group, and an unsubstituted 9,9-dimethyl fluorenyl group, and
$Ar_9$ is selected from the group consisting of an unsubstituted biphenylyl group, an unsubstituted terphenylyl group, and an unsubstituted 9,9-dimethyl fluorenyl group.

11. The aromatic amine compound of claim 1, wherein when i is 2, plural $R_6$ are combined with each other to form a cyclic structure of a saturated or unsaturated five-membered ring, which may be substituted.

12. The aromatic amine compound of claim 1, which is suitable for an organic electroluminescence device.

13. The aromatic amine compound of claim 1, which suitable as a hole injecting material or a hole transporting material in an organic electroluminescence device.

14. An organic electroluminescence device, comprising an organic thin layer comprising a single layer or plural layers including at least a light emitting layer interposed between a cathode and an anode, wherein at least one layer of the organic thin layer comprises the aromatic amine compound of claim 1.

15. The organic electroluminescence device of claim 14, wherein the organic thin layer comprises a hole injecting layer or a hole transporting layer, and the aromatic amine is in the hole injecting layer or hole transporting layer.

16. The organic electroluminescence device as described in claim 14, wherein the light emitting layer comprises styrylamine, arylamine, or a combination thereof.

17. The organic electroluminescence device of claim 14, which emits blue light.

18. An organic electroluminescence device, comprising an organic thin layer comprising a single layer or plural layers including at least a light emitting layer interposed between a cathode and an anode, wherein at least one layer of the organic thin layer comprises the aromatic amine compound of claim 5.

19. An organic electroluminescence device, comprising an organic thin layer comprising a single layer or plural layers including at least a light emitting layer interposed between a cathode and an anode, wherein at least one layer of the organic thin layer comprises the aromatic amine compound of claim 6.

20. An organic electroluminescence device, comprising an organic thin layer comprising a single layer or plural layers including at least a light emitting layer interposed between a cathode and an anode, wherein at least one layer of the organic thin layer contains the aromatic amine compound of claim 7.

21. An organic electroluminescence device, comprising an organic thin layer comprising a single layer or plural layers including at least a light emitting layer interposed between a cathode and an anode, wherein at least one layer of the organic thin layer contains the aromatic amine compound of claim 8.

22. An organic electroluminescence device, comprising an organic thin layer comprising a single layer or plural layers including at least a light emitting layer interposed between a cathode and an anode, wherein at least one layer of the organic thin layer contains the aromatic amine compound of claim 9.

23. An organic electroluminescence device, comprising an organic thin layer comprising a single layer or plural layers including at least a light emitting layer interposed between a cathode and an anode, wherein at least one layer of the organic thin layer contains the aromatic amine compound of claim 10.

\* \* \* \* \*